United States Patent [19]
Sterling et al.

[11] Patent Number: 6,049,081
[45] Date of Patent: *Apr. 11, 2000

[54] SUBSURFACE THERMAL GRADIENT SPECTROMETRY

[75] Inventors: Bernhard B. Sterling, Danville; James R. Braig, Alameda, both of Calif.; Daniel S. Goldberger, Boulder, Colo.; Charles E. Kramer, Poway, Calif.; Arthur M. Shulenberger, Brisbane, Calif.; Rick Trebino, Livermore, Calif.; Richard A. King, Berkeley, Calif.

[73] Assignee: Optiscan Biomedical Corporation, Alameda, Calif.

[*] Notice: This patent is subject to a terminal disclaimer.

[21] Appl. No.: 09/093,951

[22] Filed: Jun. 8, 1998

Related U.S. Application Data

[63] Continuation of application No. 08/820,378, Mar. 12, 1997, Pat. No. 5,900,632.

[51] Int. Cl.[7] .................................................... G01N 21/71
[52] U.S. Cl. ................................ 250/339.03; 250/252.1; 250/339.07; 250/341.6; 250/341.8
[58] Field of Search ...................... 250/252.1 R, 339.03, 250/339.04, 339.05, 339.07, 339.09, 339.11, 252.1 A, 253, 341.1, 341.5, 341.6, 341.8

[56] References Cited

U.S. PATENT DOCUMENTS 5,461,229  10/1995  Sauter et al. ............................ 250/253
5,900,632  5/1999  Sterling et al. ..................... 250/339.03

*Primary Examiner*—Edward P. Westin
*Assistant Examiner*—Richard Hanig
*Attorney, Agent, or Firm*—Lariviere, Grubman & Payne, LLP

[57] ABSTRACT

Spectrometric methodology for non-invasively obtaining optical spectra from heterogeneous material for the identification and quantification of constituent compounds. There is provided a transient or steady state subsurface thermal gradient spectroscopic methodology for obtaining in vivo optical spectra relating to the concentration of n analytes at depths to around 330 microns in human tissue, and for determining that concentration from the spectra. The methodology is employable on a wide variety of spectrometric devices, and enables: a real time determination of both surface and reference intensities; a fast, efficient calibration of the spectrometric device; and results in the provision of an analytical parameter which avoids the measurement of the optical path length to enable the extremely accurate calculation of a ratio of concentrations of n analytes in the system under analysis.

24 Claims, 12 Drawing Sheets

- Upper: Calculated "Deep Radiation"
- Middle: Drift-corrected "Target Radiation"
- Lower: Calculated "Surface Radiation"

Glucose Spectra

— Upper: Calculated "Deep Radiation"
— Middle: Drift-corrected "Target Radiation"
— Lower: Calculated "Surface Radiation"

SUBSURFACE THERMAL GRADIENT SPECTROMETRY

CROSS-REFERENCE TO RELATED APPLICATIONS

This application is a continuation of application Ser. No. 08/820,378, filed Mar. 12, 1997 now U.S. Pat. No. 5,900,632.

TECHNICAL FIELD

The present invention relates to spectrometry. More particularly, the present invention relates to a spectroscopic methodology for non-invasively obtaining optical spectra from heterogeneous material for the identification and quantification of compounds. More particularly still, the present invention teaches a transient or steady state subsurface thermal gradient spectroscopic methodology for obtaining in vivo optical spectra relating to the concentration of an analyte at depths to around 330 microns, and for determining that concentration from the spectra.

BACKGROUND OF THE INVENTION

Infrared spectrometry is an accepted and widely practiced technique for identification and quantification of compounds. The most common method of spectrometric analysis utilizes a transmission spectra. In traditional transmission spectrometry, an analysis beam of infrared light is passed through the substance being analyzed. The sample substance absorbs light in varying amounts at different wavelengths producing a transmission spectra which is a graph of the energy passed through the sample vs. wavelength. It will be appreciated that the use of transmission spectrometry generally requires that the substance being analyzed be contained in a "cell" which is placed inside the instrument for scanning. The analysis beam enters one side of the cell and exits the other. This is clearly an in-vitro technique, and is not suitable for non-invasive measurements.

In another common spectrometric technique the phenomena of Attenuated Total Internal Reflection (ATIR) is used. In this technique the sample is deposited on a plate fabricated of infrared transmissive material. The analysis beam is reflected off of this plate and back into the analyzer. At the point of reflection a portion of the analysis beam (evanescence wave) actually travels through the plate and interacts with the sample, then this portion of the beam returns to the analyzer along with the other reflected beam. A 1000 $cm^{-1}$ infrared ATIR beam typically penetrates 10 microns into the sample under study. This technique, although potentially non-invasive, is not suitable for studying the composition of deeper layers of a material.

Transmission mode measurements are ideal for gasses which transmit a large percentage of incident energy and can be easily contained in a cell. Solids and liquids are traditionally measured by using either very thin transmission mode samples or the ATIR technique. The transmission mode technique has severe limitations if the substance being measured is very dense in the wavelength region of interest. For instance if one was analyzing glucose dissolved in water or human blood the 9 to 10 micron wavelength region would be ideal however the incident analysis beam would be totally absorbed with less than 200 microns of path length. Maintaining a sample of such thin proportions is difficult. In such a case of high absorption, the ATIR technique might be useful, however, in that technique the analysis beam is only probing the surface of the substance being analyzed. The technique is useful only if the properties being measured exist at the surface of the sample.

Transmission and ATIR mode analyses are very useful in the laboratory: however if one wishes to measure something in-vivo, such as glucose in blood where even the most peripheral capillaries are covered by a typical minimum of 40 microns of epithelial tissue, clearly neither technique is adequate.

To enable in-vivo measurement of various analytes, infrared detection has been introduced in several applications. Infrared detection techniques are widely used for the calculation of oxygen saturation and the concentration of other blood constituents. For example, non-invasive pulse oximeters have been used to measure absorption signals at two or more visible and/or near infrared wavelengths and to process the collected data to obtain composite pulsatile flow data of a person's blood. Sample pulse oximeters of this type are described by Corenman et al. in U.S. Pat. No. 4,934,372; by Edgar, Jr. et al. in U.S. Pat. No. 4,714,080; and by Zelin in U.S. Pat. No. 4,819,752.

Infrared detection techniques have also been used to calculate the concentrations of constituents such as nitrous oxide and carbon dioxide in the expired airstream of a patient. For example, Yelderman et al. describe in U.S. Pat. Nos. 5,081,998 and 5,095,913 techniques for using infrared light to non-invasively measure the absolute concentrations of the constituents of the respiratory airstream of a patient by placing an infrared transmission/detection device on the artificial airway of the patient. These infrared detection techniques and those described above have proven to be quite accurate in the determination of arterial blood oxygen saturation, the patient's pulse, and the concentrations of carbon dioxide, nitrous oxide and other respiratory constituents.

Spectrophotometric methods have also been used to non-invasively monitor the oxidative metabolism of body organs in vivo using measuring and reference wavelengths in the near infrared region. For example, Jobsis describes in U.S. Pat. Nos. 4,223,680 and 4,281,645 a technique in which infrared wavelengths in the range of 700–1300 nm are used to monitor oxygen sufficiency in an organ such as the brain or heart of a living human or animal. In addition, Wilber describes in U.S. Pat. No. 4,407,290 a technique in which visible and near infrared light emitting diodes and detection circuitry are used to non-invasively measure changes in blood thickness of predetermined blood constituents relative to total change in blood thickness at a test area so as to determine the concentration of such constituents in the blood. Such constituents include hemoglobin and oxyhemoglobin, and the measured concentrations are used to determine the oxygen saturation of the blood. Wilber further suggests at columns 11–12 that such techniques may be extended to the measurement of glucose in the bloodstream; however, Wilber does not tell how to make such measurements, what wavelengths of energy to use, or the form of the mathematics necessary for the calculation of glucose concentration.

Long wavelength spectroscopic glucose monitoring techniques using infrared light are presently believed to be the most accurate and are the subject of the present application. Unlike the non-invasive oxygen saturation measurement techniques described above, prior art spectroscopic glucose monitoring techniques have typically used extra-corporeal "flow through" cells that allow continuous measurements using infrared light. Indeed, attenuated total internal reflection (ATIR) cells have been employed in the long wavelength infrared to measure the glucose content of extracted blood samples. However, as previously discussed, such techniques require samples of blood to be taken from the person and are thus undesirable for widespread consumer use.

Laser Raman Spectroscopy is another spectroscopic technique which uses a visible spectrum range stimulus and the visible red spectrum for measurement. As with ATIR cells, extra-corporeal blood is also used with Raman Technology. The Raman technique is based upon the principle that if excited with a specific wavelength certain constituents will re-emit optical energy at composition dependent specific wavelengths. Over the entire visible spectrum range whole blood has a high degree of absorption.

Another class of spectroscopic technique is described by Barnes in U.S. Pat. No. 5,070,874. According to this technique, often referred to as non-invasive near infrared spectroscopy, light is passed though a finger or suitable appendage and monitored upon exit for measuring glucose levels in vivo. Unfortunately, this technique suffers from two sources of inaccuracy: tissue interference and lack of specificity. Moreover, while the near infrared wavelengths used are easily and economically generated by light emitting diodes (LEDs) and solid state lasers, and easily transmitted through human tissue, they are not in a range specifically absorbed by glucose. This lack of "fingerprint" absorbance and interference from tissue pigment and condition render the technique unsuitable for accurate concentration determination but possibly acceptable for trending if stability can be maintained.

In an attempt to overcome the limitations of near infrared wavelengths Kaiser describes in Swiss Patent No. 612,271 a technique in which a high power infrared laser is used as the radiation source for measuring glucose concentration in a measuring cell. The measuring cell consists of an ATIR measuring prism which is wetted by the person's blood and an ATIR reference prism which is wetted with a comparison solution. $CO_2$ laser radiation, typically at 10.5 microns wavelength, is led through the measuring cell and gathered before striking a signal processing device. A chopper placed before the measuring cell allows two voltages to be obtained corresponding to the signal from the sample and the reference prisms.

Due to absorption corresponding to the concentration of the substance measured in the blood, the difference between the resulting voltages is proportional to the concentration. Unfortunately, the infrared laser used by Kaiser needs to be very powerful to get the 10.5 micron energy to pass through the blood and has the undesirable side effect of heating the blood, which may be harmful to the person if the blood were returned to the body. Although Kaiser suggests that over heating the blood may be prevented by using extra-corporeal cuvettes of venous blood and high blood flow rates, Kaiser does not describe a non-invasive technique for measuring glucose concentration.

March in U.S. Pat. No. 3,958,560 describes a "non invasive" automatic glucose sensor system which senses the rotation of polarized near infrared light which has passed through the cornea of the eye. March's glucose sensor fits over the eyeball between the eyelid and the cornea and measures glucose as a function of the amount of radiation detected at the detector on one side of the person's cornea. Unfortunately, while such a technique does not require the withdrawal of blood and is thus "non-invasive", the sensor may cause considerable discomfort to the person because of the need to place it on the person's eye. A more accurate and less intrusive system is desired.

Hutchinson describes in U.S. Pat. No. 5,009,230 a personal glucose monitor which also uses polarized near infrared light to non-invasively detect glucose concentrations in the person's bloodstream. The amount of rotation imparted on the polarized light beam is measured as it passes through a vascularized portion of the body for measuring the glucose concentration in that portion of the body. Although the monitor described by Hutchinson need not be mounted on the person's eye, the accuracy of the measurement is limited by the relatively minimal and non specific absorption of glucose in the 940–1000 nm range, dictated by the requirement of polarization, used by Hutchinson.

Mendelson et al. in U.S. Pat. No. 5,137,023 also found that wavelengths in the near infrared range are useful for non-invasively measuring the concentration of an analyte such as glucose using pulsatile photoplethysmography. In particular, Mendelson et al. describes a glucose measuring instrument which uses the principles of transmission and reflection photoplethysmography, whereby glucose measurement is made by analyzing either the differences or the ratio of two different near infrared radiation sources that are either transmitted through an appendage or reflected from a tissue surface before and after blood volume change occurs in the systolic and diastolic phases of the cardiac cycle. The technique of photoplethysmography can thus be used to adjust the light intensity to account for errors introduced by excessive tissue absorptions. However, despite the assertions by Mendelson et al., the wavelengths in the near infrared (below 2500 nm) are not strongly absorbed by glucose yet are susceptible to interference from other compounds in the blood and thus cannot yield sufficiently accurate measurements.

Rosenthal et al. in U.S. Pat. No. 5,028,787 disclose a non-invasive blood glucose monitor which also uses infrared energy in the near infrared range (600–1100 nm) to measure glucose. However, as with the above-mentioned devices, these wavelengths are not in the primary absorption range of glucose and, accordingly, the absorption at these wavelengths is relatively weak. A more accurate glucose measuring technique which monitors glucose absorption in its primary absorption range is desirable.

As with other molecules, glucose more readily absorbs infrared light at certain frequencies because of the characteristic and essential infrared absorption wavelengths of its covalent bonds. For example, as described by Hendrickson et al. in *Organic Chemistry*, 3rd Edition, McGraw-Hill Book Company, Chapter 7. Section 7–5, pages 256–264, C—C, C—N, C—O and other single carbon-hydrogen bonds have characteristic absorption wavelengths in the 6.5–15 micron range. Due to the presence of such bonds in glucose, infrared absorption by glucose is particularly distinctive in the far infrared. Despite these characteristics, few have suggested measuring glucose concentration in the middle to far infrared range, likely due to the strong tissue absorption that would attenuate signals in that range.

In one known example of such teachings, Mueller describes in WO 81/00622 a method and device for determining the concentration of metabolites in blood using spectroscopic techniques for wavelengths in the far infrared range. In particular, Mueller teaches the feasibility of measuring glucose in extra-corporeal blood samples using a 9.1 $\mu$m absorption wavelength and a 10.5 $\mu$m reference wavelength for stabilizing the absorption reading. However, Mueller does not describe how such wavelengths may be used in vivo to measure glucose concentration non-invasively while overcoming the above-mentioned tissue absorption problems. Without overcoming the large absorption by tissue in the 9 to 10 micron wavelength range, typically 90% absorption within about 30 microns of optical path in human tissue, high power infrared energy must be incident on the measurement site which can cause tissue damage and discomfort.

On the other hand, infrared emissions of bodies have been used to determine the absolute temperatures of those bodies. For example, some of the present inventors disclose a tympanic thermometer in U.S. Pat. No. 5,159,936 which measures the absolute temperature of a person from the sum total of all infrared energy emissions from the person's tympanic membrane. However, such broadband infrared energy emissions have not been used to perform constituent composition and concentration analysis.

Another prior art device developed by some of the inventors of the present invention is disclosed in U.S. Pat. No. 5,313,941 by Braig et al. In this device high intensity infrared energy of the optimal wavelength, 3 to 12 microns is passed through the finger to make a transmission mode measurement. This device requires high incident energy levels to overcome the high absorbance of tissue in this wavelength band. In this device the energy is pulsed at very low duty cycles to avoid overheating the skin.

McClelland in U.S. Pat. Nos. 5,070,242; 5,075,552; and 5,191,215 describes a method for applying a cooling medium to cool a thin surface layer portion of the material and to transiently generate a temperature differential between the thin surface layer portion and the lower portion of the material sufficient to alter the thermal infrared emission spectrum of the body from the black-body thermal infrared emission of the material. The altered thermal emission spectrum is detected while the emission spectrum is sufficiently free of self-absorption by the material of the emitted infrared radiation. The detection is effected prior to the temperature differential propagating into the lower portion of the material to an extent such that the altered thermal infrared emission spectrum is no longer sufficiently free of self-absorption by the material of emitted infrared radiation. By such detection, the detected altered thermal infrared emission spectrum is indicative of the characteristics relating to the molecular composition of the homogenous material.

Transient thermal emission spectrometry, for instance as taught by McClelland in U.S. Pat. No. 5,075,552; and by Imhof, (SPIE Vol.2329), is useful for the analysis of surface layer composition. Such spectrometry has also been applied to in-vivo skin research. Heat (in the form of radiation or hot gas) is applied to a surface and an emission spectrum is measured that contains spectral information about molecular composition of several conventional transmission spectrum. Spectra of respectable quality have been obtained by this methodology. Further, depth profiling has been carried out by time-resolved use of a laser at different wavelengths and different thermal penetration depths as a function of time. Radiation intensity is absorbed exponentially with depth leaving much more energy in the surface layers. A significant fraction of the absorbed energy is emitted from that surface layer without being "self-absorbed" again. It is this phenomenon of emission emanating largely from the immediate surface layer, that limits the usefulness of the emission technology to the top surface. This is because these emissions contain only specific spectral content of the top surface layer. Analysis of the deeper layers is also hampered by this, and a second effect: Specific emissions from deeper layers are self-absorbed by the top layers of material closer to the surface and are thereby largely converted to a non-specific blackbody emission. Thus, transient thermal emission spectrometry may be useful for top surface analysis but offers less potential for subsurface layer compositional analysis.

A possible solution to the shortcomings of previous transient thermal emission spectroscopic methodologies as used for subsurface layer compositional analysis lies in the fact that a natural thermal gradient exists across human skin between the body's core temperature of close to 37° C. and the skin surface temperature. Skin temperature is largely determined by skin capillary perfusion and temperature of the extraneous material in contact with the skin, e.g. air, fabric, solid material. The natural gradient is however small, sometimes no more than 1 degree Celsius per millimeter. However it can be substantially enlarged transiently or steady-state by the application of heat to the skin followed prior to or simultaneous to efficient heat withdrawal.

For analysis of the composition of subsurface layers, such as human skin for example, there are several advantages to using transmission spectrometry rather than emission spectrometry. In contrast to thermal emission spectrometry, in thermal gradient transmission spectrometry (whether transient or steady-state), the contribution of the immediate top surface layer to the overall transmission spectrum is relatively small because 1) it is the coldest layer and therefore contributes the smallest amount of blackbody radiation of all layers, 2) it is too thin to provide sufficient optical depth in many cases and 3) it's absorptive characteristics are not necessarily larger than those of deeper layers. Transient thermal transmission spectrometry has also been described by McClelland (5,070,242), and by some of the inventors of the present invention in co-pending U.S. patent application Ser. No. 08/544,267. This technique holds significant promise for the accurate, non-invasive measurement of in-vivo physiological constituents, if certain problems inherent in the interpretation of raw radiometric data provided thereby can be overcome. Further, the technique may be useful for other non-invasive metrologies, including but not necessarily limited to the measurement of materials through packages, e.g. food packages, and the measurement of blood pH.

To put these problems into perspective, it should be noted that thermal gradient spectrometry is similar in concept to conventional un-referenced single beam transmittance spectrometry with a simultaneous continually dimming light source and variable cuvette depth. From these facts, it is clear that several major problems exist in the interpretation of the raw radiometric data from an infrared source.

At any wavelength the total infrared emission $I_t$ reaching a detector, for instance the detector of an infrared spectrometer, can be defined as:

$$I_t = I_i + I_r + I_s + (I_0 * T),$$

where $I_i$ is the instrument background emission intensity,
  $I_r$ is the reflected emission,
  $I_s$ is the surface emission,
  $I_0$ is the reference intensity,
  and T is the transmittance, generally defined as the ratio $I/I_0$.

The Problems of $I_0$ and $I_s$

One major problem in the interpretation of transient or steady-state thermal gradient subsurface spectrometric data is in the determination of the Reference Intensity $I_0$. If one approximates the material to be analyzed as consisting of layers of equal or variable composition, then $I_0$ is the total integrated emission from all the deep layers before modification by absorption in each individual layer. The reference intensity is produced while the thermal gradient exists, and is radiated out of the material under analysis, then convoluted with the instrument response function without the self-absorption effect of the cooler surface layer and without emission from the surface. In conventional spectrometry $I_0$ is simplified as just the energy source intensity and approximated by a separate measurement. In transient or steady-state thermal gradient spectrometry the integral parts of $I_0$ are the effective emission intensity, as well as the blackbody and specific spectral emissions coming from the deeper layers of the material during the thermal gradient.

Further, there is a surface emission $I_s$ directly from the surface of the material under analysis. It consists of both blackbody and spectral emissions. A theoretically separate component from the surface is reflected emission $I_r$. Surface emission is not part of $I_0$; that is to say that it has not gone through the colder absorptive layer, and therefore it is not modified by self-absorption. Although surface emission is variable in intensity during the gradient as the surface is being cooled, it is possible to define an effective surface temperature during a time element.

The quality of $I_0$ and $I_s$ measurements are as important as the quality of the sample intensity I measurements in determining the analytical accuracy of the constituent of interest. As the thermal gradient progresses to the deeper layers, the intensity and wavelengths of the emission peak of the initial blackbody radiation are dynamically changing. These layers are not only cooled in the process but their radiative emission is both substantially decreased and shifted to longer wavelengths. For non-intrusive in-vivo measurements, the actual effective temperature is inaccessible to physical measurements with a temperature probe. Nonetheless, it is necessary to know the effective deep layer emission or equivalent deep temperature because it is needed to calculate the effective deep, or reference intensity $I_0$.

Transmittance is generally defined as the ratio $T=I/I_0$. Accordingly, the quality of the $I_0$ measurement or semi-empirical determination yields the resolution and accuracy of the resulting analytical constituent calculation. In addition to the emission from the material of interest there is the emission intensity $I_i$ from instrument components. Since $I_t=I_i+I_r+I_s+(I_0*T)$, it becomes apparent that transmittance can only be calculated properly after the intensities emitted from the surface and from instrument components have been determined and subtracted.

By taking the ratio of $I_t/I_0$, with $I_0$ being the result of an approximate determination, it is relatively easy to obtain an approximate transmittance spectrum that may be sufficiently accurate for less demanding applications, such as taught by McClelland U.S. Pat. No. 5,070,242. In fact for many applications, such as simple mixtures of relatively few components present in large relative amounts such a simple treatment may be perfectly satisfactory. With more critical metrology however, the use of this approximation leads to erroneous results. This is particularly true in applications with samples having relatively many components and which contain small amounts of one or more components that need to be measured accurately, such as clinical determinations of glucose or alcohol concentrations in body fluid. It is also true in applications that require larger percentages of components to be measured very accurately. Mathematically and physically, the problem lies in an incomplete elimination of all interfering emissions that originated either from any surface and/or from the deeper layers of the material during the thermal gradient.

The simplistic approach of taking a ratio will, by definition, give an exact transmittance spectrum only when all components that contribute to $I_t$ are exactly accounted for. This can only occur if and when the individual components can be determined independently from the superposition of the relative contributions from blackbody radiation and the emission/absorption depth dependent information. In conventional spectrometry the problem of sufficiently exact measurement of $I_0$ and $I_t$ was largely solved when dual beam and/or highly stabilized energy source and detector systems were invented. A major limitation to accuracy improvements in conventional spectrometry is the fact that the reference measurement cannot be taken from the actual measurement energy while the measurement is taken without disturbing the measurement itself.

Neither the experimentally calculated deep emission nor the calculated surface emission are truly blackbody radiations, but rather are essentially blackbody radiations with specific spectral emission components superimposed onto them. It is appropriate, however, to treat them as blackbodies because the specific components are exactly the mirror images of the transmittance spectra of any layer of the material being analyzed. These spectral emission components are small in comparison to the effective absorption components induced by cooling and simply reduce the magnitude of the final transmission spectra without distorting them.

Several approximations for $I_0$ may be useful in spectrometry less critical than in-vivo titer analysis. These include, but are not necessarily limited to:

1) The utilization of a reference scan that is taken in a timely manner before the surface is cooled while the thermal infrared emission spectrum is substantially free of self-absorption, as taught by McClelland in U.S. Pat. No. 5,070,242.

2) Alternatively, one may try to experimentally approximate the deeper layer gradient temperature emission by measuring the sample at different temperatures without a thermal gradient and subsequently use the one scan that gives the best approximation as judged from the results.

3) As a further alternative, one can physically measure the surface temperature and the core temperature of the material, and thereafter derive an effective deeper layer radiation intensity by interpolation from the gradient temperature-depth profile. These temperatures can be converted to intensities by applying Planck's function.

What is really required however to enable the use of thermal gradient spectrometry as an accurate diagnostic technology is a novel method that reveals the effective $I_0$ more accurately than any of the preceding approximations.

Because the prior art does not teach an accurate measurement methodology for $I_0$, or even the importance thereof, the work of others does not, in general, teach:

1) how to use wavelength ranges in a semi-empirical fashion such that the effective deeper gradient layer emission intensity and blackbody-equivalent emission temperature can be derived and can subsequently be used as the reference or standard intensity $I_0$ in the calculation algorithm for transmittance;

2) the importance, determination and elimination of the effects caused by variable contribution of surface emission in the determination and spectral calibration for 0% transmittance;

3) the separation of deep layer radiation and surface emission; nor 4) the utilization of wavelength ranges for the best possible spectral calibration for 100% transmittance calculation.

The Problems of Calibration and Instrument Drift

All radiometers, including spectrometers, require calibration. Further, instrument settings can change over time, resulting in an error-inducing "drift". These facts are especially significant in transient thermal gradient transmission spectrometry, where a single "reading" is actually a continuous series of readings which result in a whole value. Ideally, a radiometer should be calibrated between individual measurements, and any drift corrected for. Since a single transient thermal gradient transmission spectrometric reading is an event measured in fractions of a second, and composes a number of individual measurements, a means for calibrating the instrument in near real time will render substantial improvements in instrument accuracy over previous thermal gradient transmission spectrometric methodologies. Similarly, a methodology for compensating, again in near real time, for any instrument drift which accumulates will significantly improve the accuracy of previous efforts at thermal gradient spectrometric constituent analysis.

The Optical Path Length Problem

Another major problem not contemplated by the prior art in the interpretation of transient or steady-state thermal gradient spectrometric data is in the determination of the optical path length. In conventional terms optical path length is equivalent to the cuvette dimension through which the light beam is traveling. In thermal gradient spectrometry there is no strictly defined cuvette thickness. In fact, effective cuvette thickness increases continually as the thermal gradient develops. The useful range though, is only a few optical depths, defined as the distance after which any intensity is reduced to 1/e by absorption. The equivalent in conventional terms would be a cuvette that increased in dimension while the measurement is being taken. According to Beer's law, which can be applied as the simplest case, $$-\log \frac{I}{I_0} = \beta c L$$

where:
  $\beta$ is the absorption coefficient;
  c is the concentration of a constituent, such as glucose;
  and L is the optical path length.

It is immediately apparent, using this classical application of Beer's Law, that the concentration c cannot be determined if the path-length L is unknown. A methodology which allows the determination of a parameter whereby the concentration c of an analyte can be ascertained without the necessity for making an explicit determination of path-length L would finally enable transient thermal gradient spectrometry as a precision measure of such concentrations.

Summarizing the preceding discussion, thermal gradient spectrometry (either transiently or steady-state) holds promise as a methodology for obtaining in vivo optical spectra relating to the concentrations of analytes at depths to around 100–200 microns, and for determining those concentrations from the spectra. To fulfill this promise certain problems must be overcome and certain relationships defined. None of these solutions, unfortunately are taught or suggested by the cited reference. Specifically, what is required is:

a. Explicit, real time determination of $I_0$ and $I_s$.
b. Fast, efficient calibration of infrared spectrometer.
c. A relationship like the Beer-Lambert Law between light intensity and analyte concentration which is operative for thermal gradient spectrometry (TGS).
d. Determination of a parameter which avoids having to measure path length explicitly.
e. A means for determining a ratio of the concentrations of n analytes within a solution of analytes.

A technique for the non invasive measurement of physiological constituents, specifically glucose, must address the problems that tissue is heterogeneous in composition with the tissue layers containing the physiological concentration of interest laying 20–150 microns below the surface. Furthermore, the technique must assure a safe and effective measurement that will not cause temporary or permanent damage to the surface or underlying tissues in the measurement site nor cause discomfort to the human subject. The technique must also overcome the potential problem that glucose and other physiological constituents are present in combination with a number of other similar molecules and must be distinguished for accurate quantification. Ideally such a technique would not require a high power source of infrared energy so that a device could be made portable and lightweight.

DISCLOSURE OF INVENTION

The following description is presented to enable one of ordinary skill in the art to make and use the invention as provided in the context of a particular application and its requirements. Various modifications to the preferred embodiments will be readily apparent to those skilled in the art, and the generic principles defined here may be applied to other embodiments. Thus, the present invention is not intended to be limited to the embodiments shown, but is to be accorded the widest scope consistent with the principles and novel features disclosed herein.

The present invention provides a method for the reduction of Transient or Steady-state Thermal Gradient Spectrometric data to highly accurate conventional transmittance or absorption spectra. Thermal gradients have a depth of penetration into the material, and the depth of penetration defines the optical pathlength under analysis. The disclosed method is particularly useful for the measurement of low-level constituents in mostly aqueous multi-component systems such as live skin. Thermal gradient spectrometry is, by the nature of the phenomena, a superposition of highly variable emission/absorption spectral information that is grossly influenced by the transient thermal gradient's continually changing blackbody radiation. The disclosed method produces data that are essentially free of such interfering blackbody radiation.

The present invention teaches several improvements to thermal gradient spectrometry, particularly as applied to the use of thermal gradient spectrometry to determine in-vivo analyte concentrations, as well as a methodology for determining the ratio of concentrations of n analytes. To accomplish these improvements and features, the present invention further teaches methodologies for the a. Explicit, real time determination of $I_0$ and $I_s$.
b. Explicit near real-time determination of $I_r$ and $I_i$, thereby enabling the fast, efficient calibration of infrared spectrometric equipment.
c. Determination of a parameter which avoids having to measure path length explicitly, which enables the definition of a relationship similar to the Beer-Lambert Law between light intensity and analyte concentration which is operative for TGS.
d. From the foregoing relationship, a methodology for determining a ratio of the concentrations of n analytes within a solution of analytes.

The succeeding discussion centers around the use of well known spectrometric equipment, modified as noted herein to obtain the advantages taught. Applicants note that these advantages are best achieved with a special-purpose thermal gradient spectrometric device, for instance as taught and shown in the patent application entitled NON-INVASIVE INFRARED ABSORPTION SPECTROMETER FOR THE GENERATION AND CAPTURE OF THERMAL GRADIENT SPECTRA FROM LIVING TISSUE and identified by attorney's docket number P681, further known as U.S. patent application Ser. No. 08/816,723, filed Mar. 12, 1997, and filed internationally as International Patent Application No. PCT/US98/04809 on Mar. 10, 1998, which is hereby incorporated by reference.

The spectrometric method taught therein for the non-invasive generation and capture of thermal gradient spectra from living tissue comprises the steps of:

cooling an infrared transmissive mass;

placing the infrared transmissive mass into a conductive heat transfer relationship with the tissue thereby to generate a transient temperature gradient in the tissue;

detecting infrared emissions emanating from the tissue and passing through the infrared transmissive mass;

providing output signals proportional to the detected infrared emissions; and sampling the output signals as the transient temperature gradient progresses into the tissue.

To obtain these advantages for a given subject, a thermal gradient (a temperature event) is induced and a measurement is taken at a first well-chosen wavelength or set of well-chosen wavelengths with a spectrometer. Then, using this measurement and Planck's Law, $I_s$ is calculated for all wavelengths.

Further to the temperature event, a measurement is also taken with the spectrometer at a second well-chosen wavelength or second set of well-chosen wavelengths. Then, using this second measurement and Planck's Law, $I_0$ is calculated for all wavelengths.

Spectrometer measurements are also taken at all wavelengths immediately before and after a temperature event. These measurements are then used to create correction functions for $I_t$ and $I_r$. The voltage output of the spectrometer sensor are thus translated into watts.

Finally the ratio of transmittances at two or more different, well-chosen wavelengths is calculated, for instance using a digital computer including processing device, memory device, bus device and I/O device. The ratio of transmittances can then be correlated to the ratio of concentrations of n analytes of the sample under analysis.

Accordingly, the present invention specifically teaches:

1) how to use wavelength ranges in a semi-empirical fashion such that the effective deeper gradient layer emission intensity and blackbody-equivalent emission temperature can be derived and can subsequently be used as the reference or standard intensity $I_0$ in the calculation algorithm for transmittance;

2) the importance, determination and elimination of the effects caused by variable contribution of surface emission in the determination and spectral calibration for 0% transmittance;

3) the separation of deep layer radiation and surface emission; and 4) the utilization of wavelength ranges for the best possible spectral calibration for 100% transmittance calculation.

The present invention discloses semi-empirical approaches that are useful in general for the reduction to conventional data or transmittance spectra. The procedure has been optimized for systems that contain large relative amounts of water. There is wider applicability to homogeneous and especially heterogeneous and layered materials providing that useful wavelength ranges can be identified.

The invention disclosed herein can be utilized with a variety of infrared radiation detecting systems and is in no way limited to a Fourier Transform Infrared instrument. The invention can be adapted to a wide variety of instrumentation systems, to a wide variety of solid or semi-solid materials that need to be analyzed for constituents, and to a variety of analytical approaches ranging from a series of strictly defined mathematical steps to multi-parameter regression methods. The methodology taught herein is particularly applicable to, but not limited to, the analysis of a heterogenous material composed of a plurality of constituents, at least one of which, as a material of interest, is an analyte. It is in fact possible to use chemometric or other powerful multi-parameter approaches, such as neural networks, directly on specific spectrometric data for constituent analysis and find an acceptable solution to the problem. If however, in any of such complex approaches, wavelength ranges are utilized that in effect constitute a) a determination and/or elimination of surface emission, and/or b) an implicit or explicit determination of deep layer emission, it would fall under the scope and spirit of the present invention.

It should be noted that alternative wavelength ranges can also be utilized in the determination of the concentration of water in the material. The relative plateau from about 7 to 10 $\mu$m is useful for a relative water determination at any wavelength where constituents other than water show relatively little absorbance. Alternatively, the constituent of interest can be related to one other major constituent that is essentially constant in its relative amount. Total protein is such a candidate; it shows several strong absorbencies in the wavelength range from about 6 to 8 $\mu$m. Particularly in skin, total protein is not expected to change much.

Subsequent to calculation of this ratio, it can be transmitted, for instance as an output electrical signal by the computer, for further use. Such uses include, but are specifically not limited to display devices, further data processing devices, diagnostic or clinical devices, or any other device whereby the ratio is displayed, processed or further utilized. Further, while the output signal may preferably be electrical in nature, alternative signal transmission methodologies are also contemplated by the teachings of the present invention. Such alternative signal transmission methodologies include, but are specifically not limited to: optical signals; mechanical signals, visual signals, pressure signals, and other signal transmission methodologies well known to those of ordinary skill in the art.

Other features of the present invention are disclosed or apparent in the section entitled "BEST MODE OF CARRYING OUT THE INVENTION".

BRIEF DESCRIPTION OF THE DRAWINGS

For fuller understanding of the present invention, reference is made to the accompanying drawing in the following detailed description of the Best Mode of Carrying Out the Invention. In the drawing.

Figure 1:
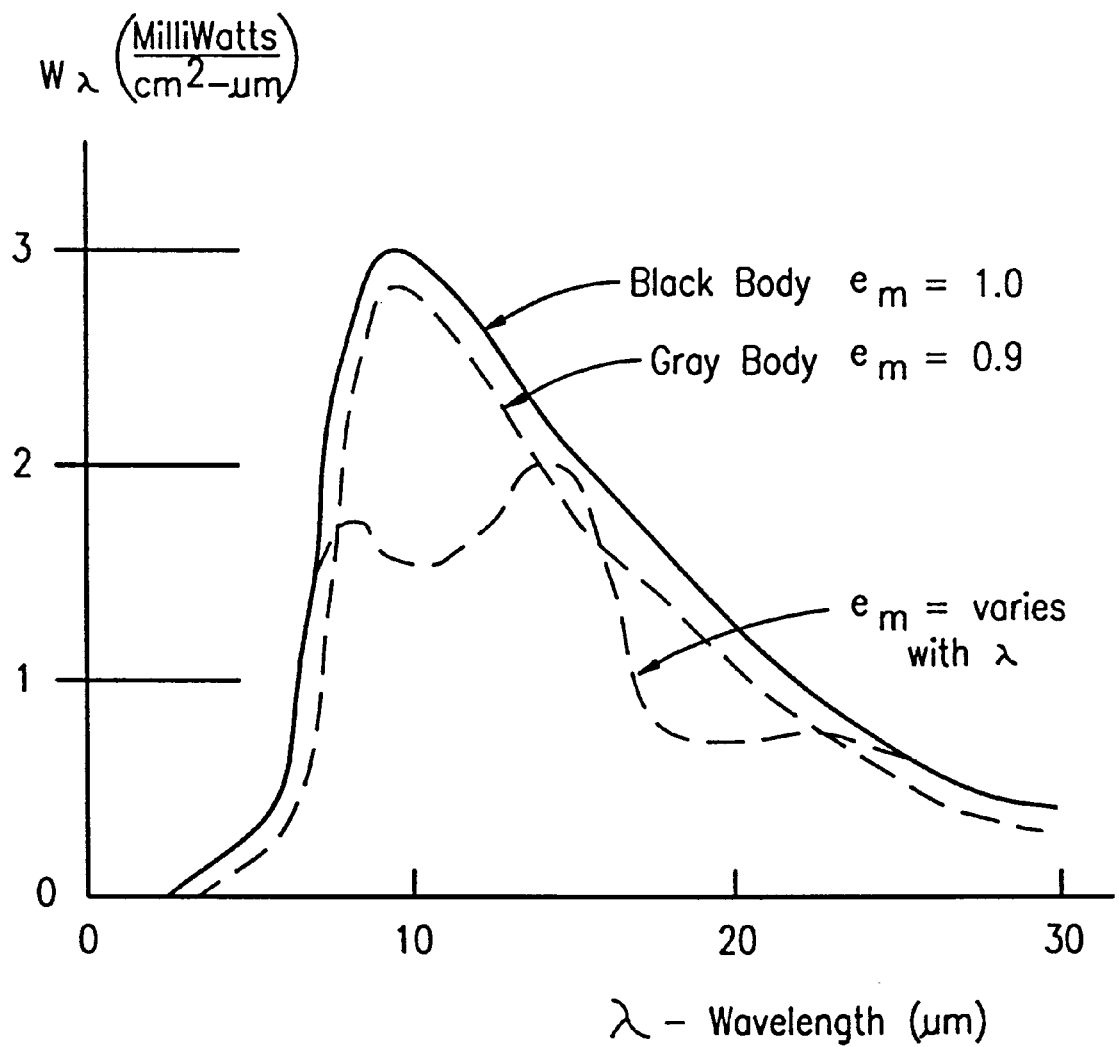
FIG. 1 is a graph of a black body emission spectra from a heated body.

Reference numbers refer to the same or equivalent parts of the invention throughout the several figures of the drawing.

BEST MODE OF CARRYING OUT THE INVENTION

Any object at a temperature above absolute zero (−273.16 Degrees Celsius) emits infrared energy. The energy density of such emissions is described by Planck's law:

W=em*Fn ($\lambda$,t)

Where:

W=energy in watts/cm$^2$ per micron em=emissivity

Fn=a mathematical function with variables $\lambda$ and t $\lambda$=wavelength of emitted energy, in microns t=temperature of the emitting body, in degrees Kelvin The full form of this equation is:

W=em*(3.74E4/{$\lambda^5$*[(exp(1.438E4/($\lambda$*t))−1]})

The graph of these emissions vs. wavelength is often referred to as a blackbody curve. Such a curve is shown in FIG. 1. Theoretically, a body with emissivity 1.0 would exhibit this emission spectra according to Planck's law. Many objects do have emissivities close to 1.0. Human tissue for instance has an emissivity of approximately 0.9 to 0.98. It is well known that infrared emissions from the human body obey Planck's law and yield a black body type emission spectra.

Although a human body may emit energy that follows Planck's law, Planck's law does not completely describe the sum total of all energy emitted from a human body for two reasons:

1. The layers of the tissue and body fluids are selectively absorptive to some wavelengths of infrared energy. Thus layers of tissue and blood or other fluids may selectively absorb energy emitted by the deeper layers before that energy can reach the surface of the skin.

2. There is a temperature gradient within a body, the deeper layers being warmer than the outer layers which causes further deviation from the theoretical black body emissions.

Whenever these two conditions exist naturally, or can be forced to exist, Applicants have determined that a composition dependent absorption spectra can be constructed from proper analysis of the total energy emitted from the body. For heterogeneous bodies, composition may be depth dependent and conversely, absorption spectra generated from deeper layers can contain sufficient composition information to allow quantification of the concentrations of individual constituents at that depth into the tissue. This is possible when a temperature gradient either occurs or is induced in the body. The slope of the temperature gradient is such that the temperature is cooler at the surface of the body closer to an infrared detector than at a more distant location from the detector, typically deep within the body.

The present invention uses the natural heat within the body as the source of the infrared emissions. The natural emissions of the present invention are merely black body emissions fitting Planck's equation—they do not contain any composition dependent structure. As these deep infrared emissions pass through layers of tissue that are at a lower temperature than the deeper emitting layer they are selectively self absorbed. This selective self absorption produces bands of reduced energy in the resulting emission spectra when the energy finally exits the material under study. The spectra containing the bands where energy has been self absorbed is called an absorption spectra.

The present invention employs cooling to promote "self-absorption" by letting the temperature gradient propagate to selected layers typically between 40 and 150 microns below the surface. When the temperature gradient has sufficiently propagated, the present technique can, non-invasively, deliver absorption spectra of the tissue, blood, and interstitial fluid containing glucose or other analytes. The present invention can deliver precise information about the composition of individual layers deep within a heterogeneous body of material by measuring the absorption spectra at different times as a temperature gradient propagates from the surface to deep within the material under test.

Figure 2:
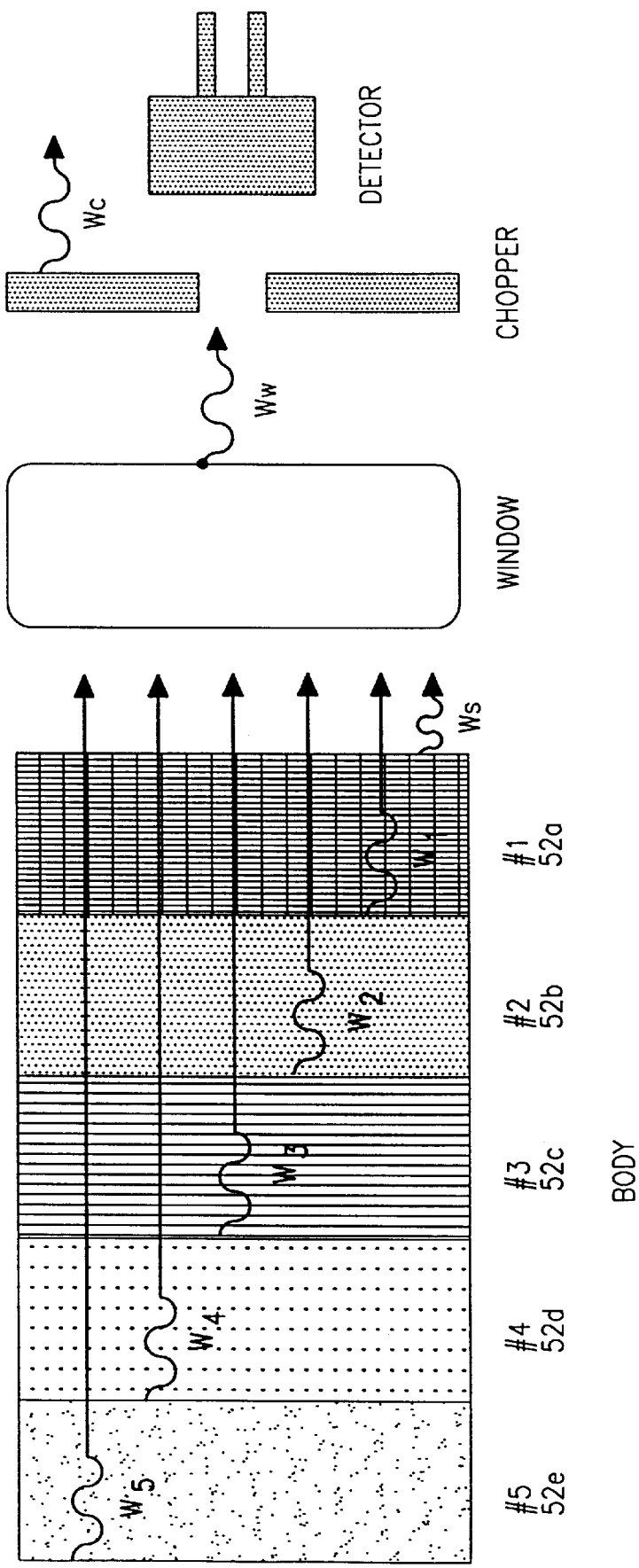
FIG. 2 is a block diagram of a typical body that includes multiple layers.

Referring now to FIG. 2, a conceptual explanation for the phenomenon in accordance with the present invention will be described below. Consider for the sake of explanation the case of human skin. It is known that in a typical forearm the core temperature is approximately 37° C. and the external surface is typically at 30° C.

To simplify our conceptual model consider that the skin is made of many layers each approximately 10 microns thick. Let's further simplify our model in FIG. 2 by assuming that each layer 52a–52e in the model emits energy according to Planck's equation based on the temperature of that layer 52a–52e. A detector system 54 looking from outside can observe that radiation. The outermost layer 52a emits energy that travels directly to the detector 54, energy from the outer layer 52a does not pass through any other layer 52b–52e on its route to the detector 54. Energy from the second layer 52b inward must pass through the first layer 52a before exiting the tissue and passing on to the detector 54. As the energy from the second layer 52b enters the first layer 52a it is selectively absorbed by the compounds present in the first layer 52a. This absorption is just like the absorption that takes place in the classical transmission cell spectroscopy apparatus. The first layer 52a absorbs the energy from the second layer 52b selectively—at specific wavelengths.

The total energy radiated from the subject appears very much like conventional black body emissions. However, if careful observation is made, the difference between a black body emission spectra and the emissions after absorption by deeper layers when an internal temperature gradient exists, subtle but important differences can be observed. The model of FIG. 2 was implemented using typical numbers and produced the output shown in FIGS. 3a and 3b.

Figure 3A:
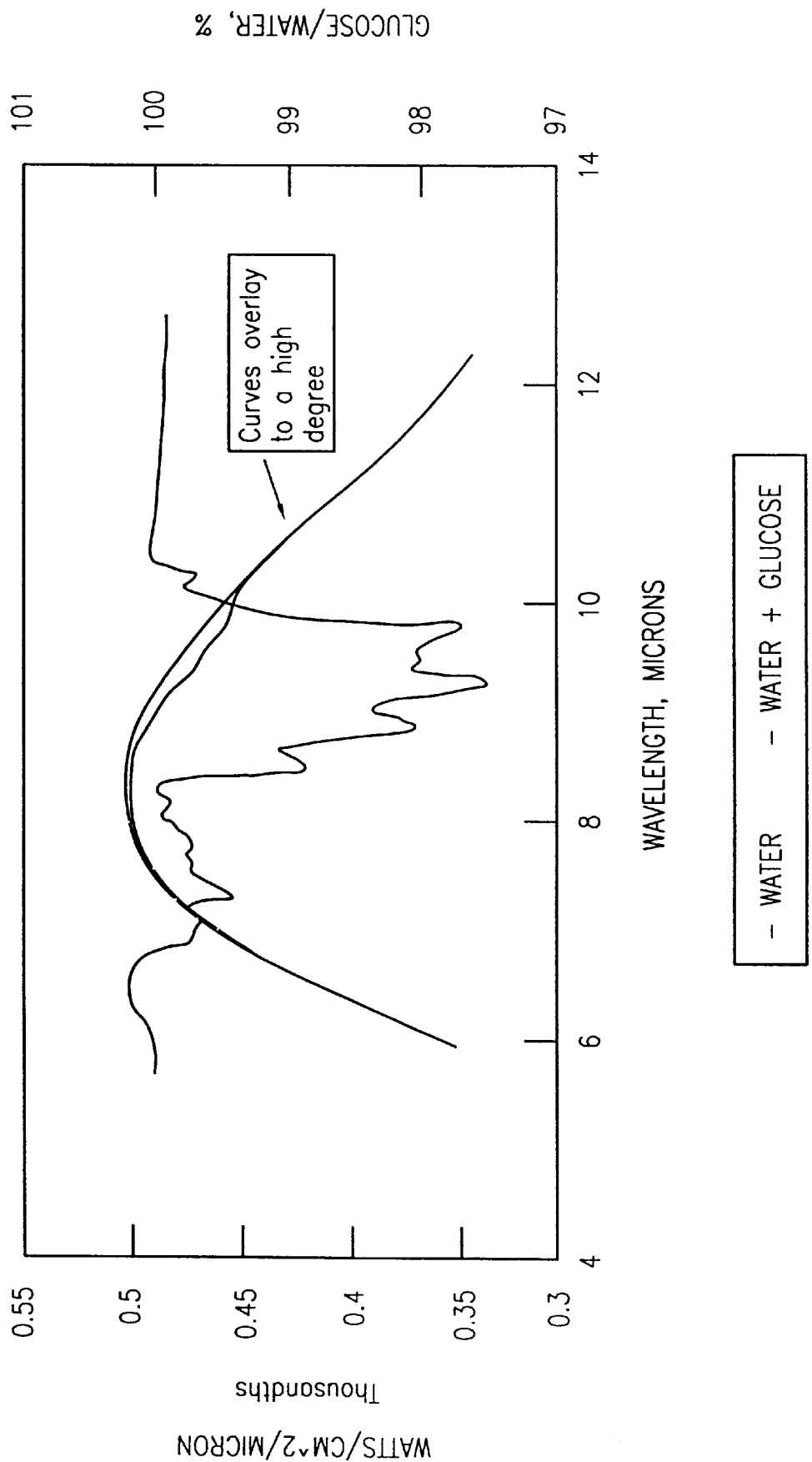
FIG. 3a is a diagram of an emission spectrum of a constituent in a body, when the body has a thermal gradient.
Figure 3B:
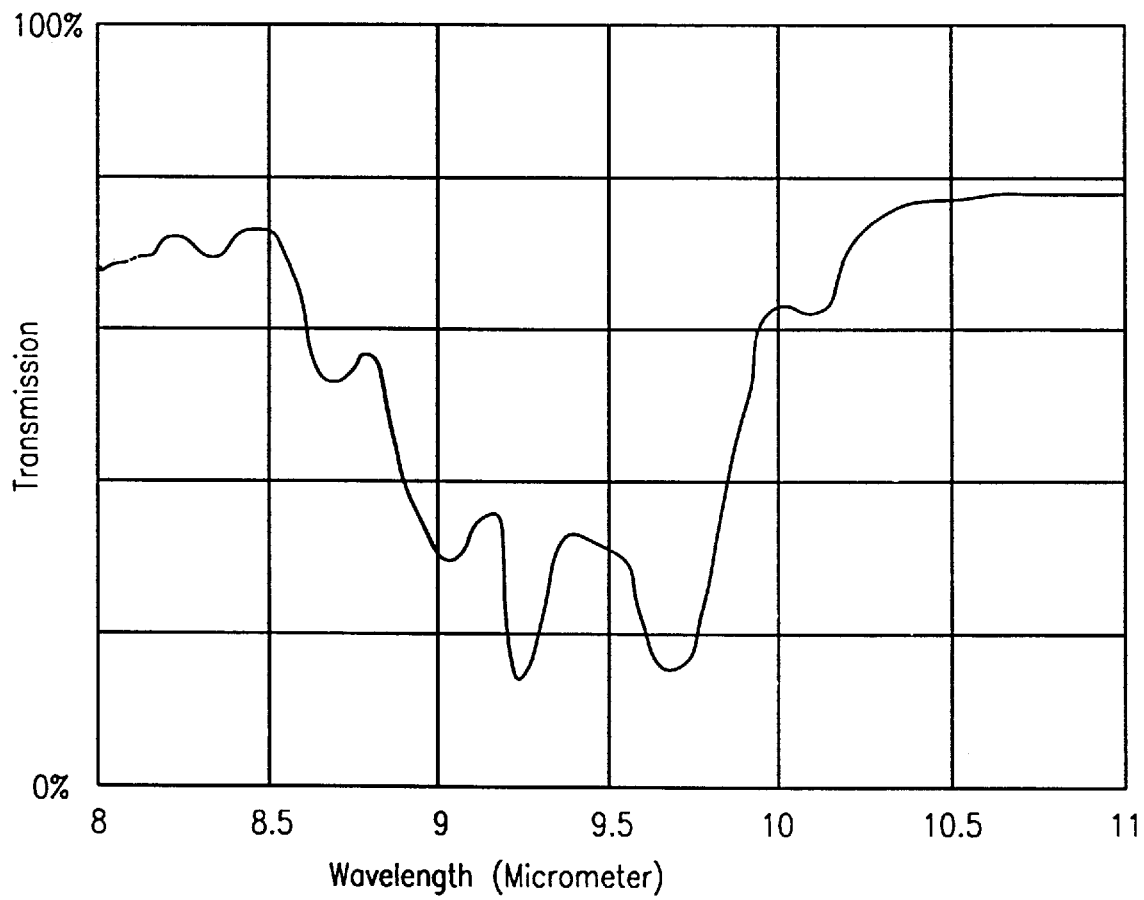
FIG. 3b is an absorption spectra of glucose produced using conventional transmission spectroscopy.

With this model, for illustrative purposes two spectra are shown in FIG. 3a, one for water and one for water with glucose dissolved in it. In normal physiological concentrations of glucose both spectra would look very similar to the Planck emission curves describing a black body and would be nearly overlapping. However, with high concentrations of glucose in solution (5%) a small perturbation near 9 microns can be observed. When the ratio of the glucose solution to the pure water emission spectra are taken the characteristic glucose absorption spectra emerges. The magnitude of the spectra depends on the glucose concentration and the temperature gradient. The gradient induced glucose spectra compares favorably with the conventional transmission spectra of glucose shown in FIG. 3b.

In order to elucidate spectral absorption of constituents of bodies where the presence and concentration of the constituent varies by depth below the surface it is necessary to establish and control the magnitude, propagation velocity and contour profile of the thermal gradient described previously. The above-identified model addressed only the absorption of layers of homogeneous material subjected to a large steady state thermal gradient. One purpose of this invention is to dynamically establish and control the magnitude and propagation depth of a thermal gradient to elucidate selectively (as a function of time and depth) the thermal absorption of the deeper layers below the surface within which the concentration of the tissue constituent is of physiological interest.

Figure 4:
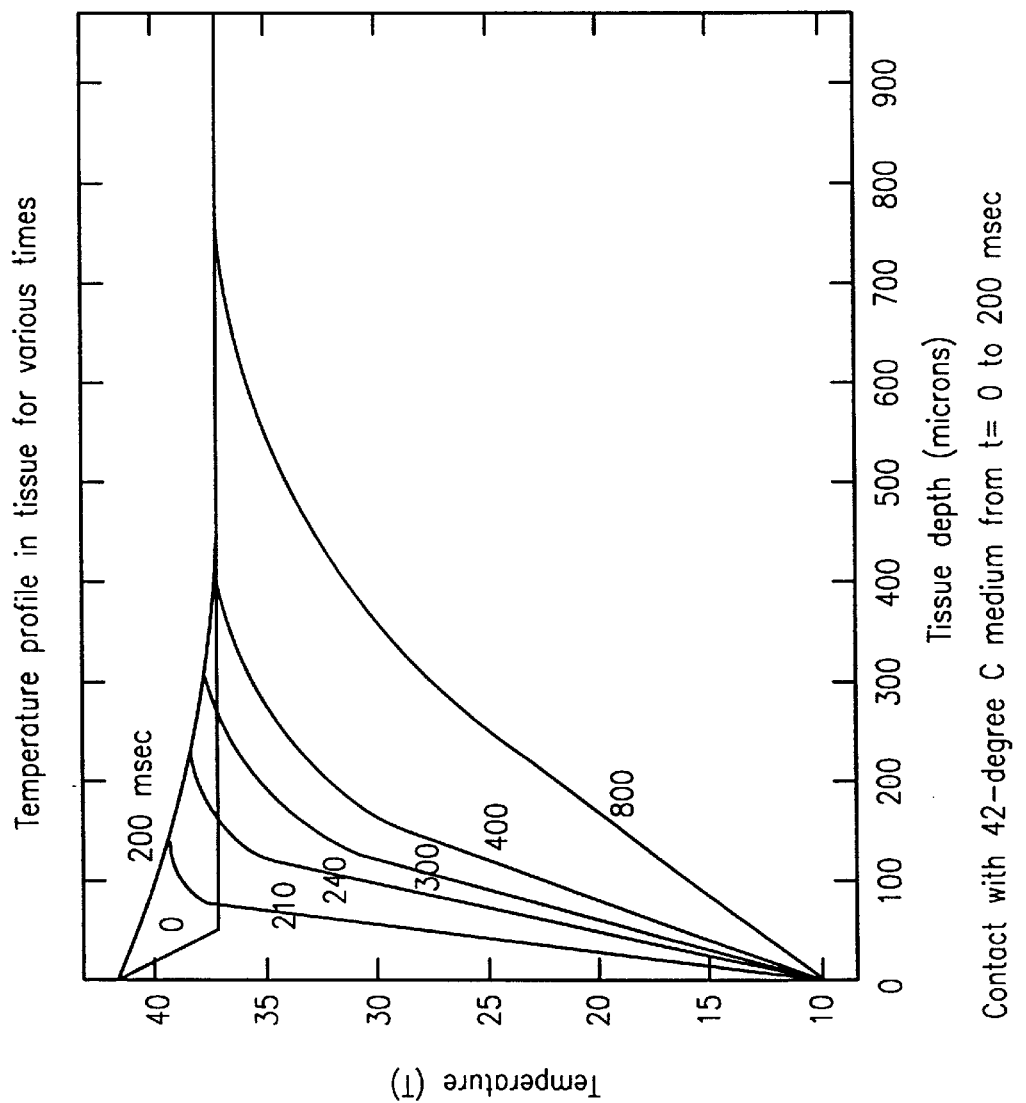
FIG. 4 is a curve that shows the depth profile of the gradient at different points in time.

The infrared spectral content of absorption by subsurface layers will be directly related to the magnitude of the gradient existing (i.e., induced) across the layer. The magnitude of the gradient will vary from near zero before the thermal gradient has propagated to that layer to a maximum value approximately defined by the difference between the high temperature within the body and the low temperature at the surface of the body divided by the thermal gradient depth. FIG. 4 also describes the three variables of the dynamics associated with the time dependency of establishment, propagation and thermal gradient contour profile induced into a body. FIG. 4 describes the influence of the gradient interacting with depth dependent concentrations of the constituents of interest, and FIG. 5 the corresponding infrared spectral emission pattern. The thermal gradient contour profile is a three dimensional representation of the above concepts.

Figure 5:
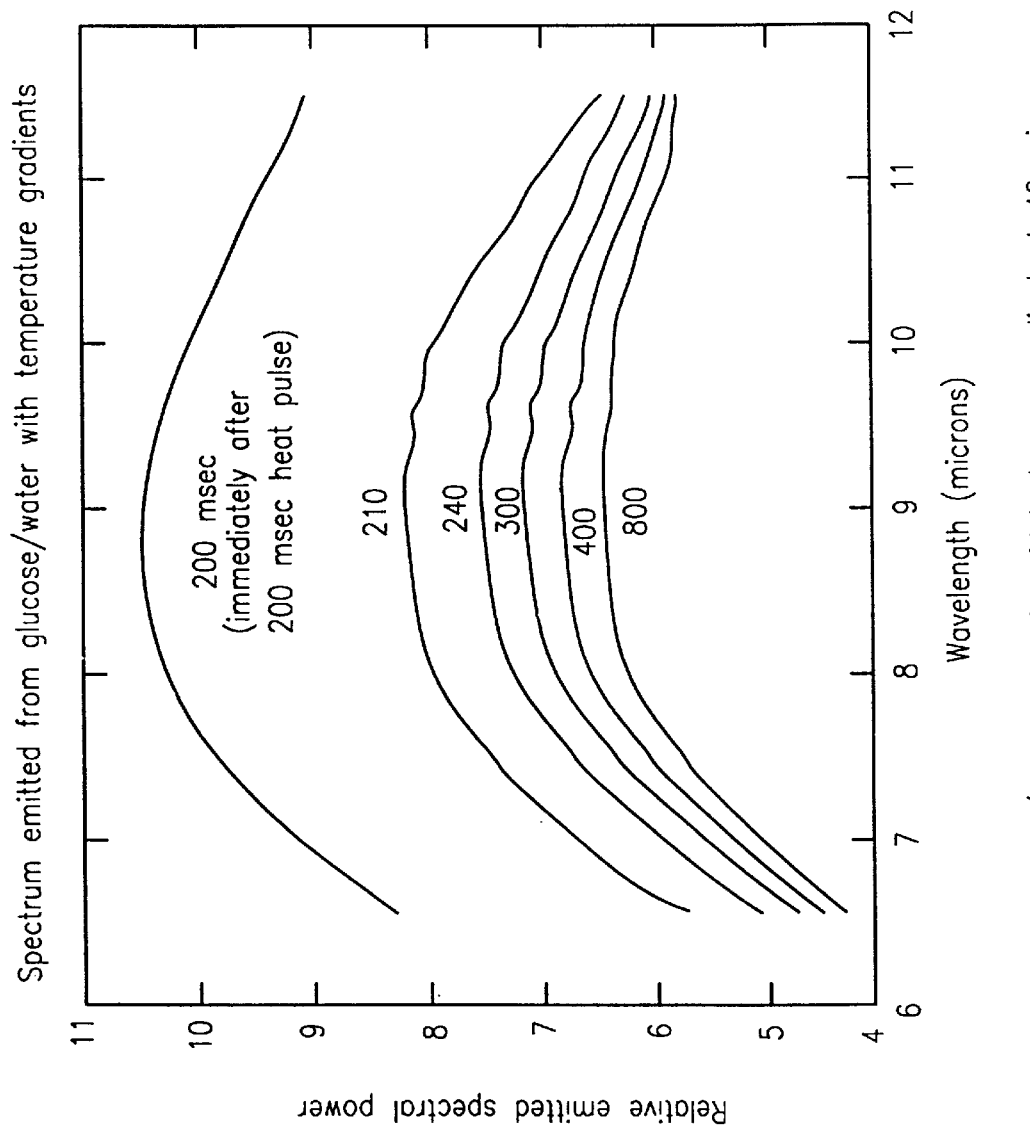
FIG. 5 is a curve which illustrates the time dependency of the spectral content of the emission pattern.

The resultant time (depth) dependency of the spectral information, shown in FIG. 5, illustrates that in human tissue the spectral content of interest will not begin to appear in the infrared absorption until approximately 100 ms (milliseconds) after cooling the external surface has begun and will transiently increase in intensity with a maximum occurring between 125 to 175 ms. After which the spectral content will decrease until approximately 200 ms. The decrease is due to the accumulative effects of both optical absorption as a function of increasing depth and to the change in its profile (the decrease in the magnitude of the gradient).

In order to optimize the thermal gradient in magnitude, propagation velocity, and contour profile, the thermal boundary conditions and thermal conductive properties of the means for heating and cooling the body must be considered. The considerations are particularly important for physiological application of the invention wherein the body refers to the human body and avoidance of temporary or permanent damage to the tissue is paramount. The maximum temperature to which human tissue can be subjected for prolonged or repeated exposure is 41–42° C. The minimum temperature is less well defined but estimated at −3° C. for transient exposure of 1–2 seconds.

One mechanism or process for creating and controlling the magnitude, propagation velocity and contour profile of the thermal gradient incorporates cyclic cooling and re-warming of the observation site. The mechanism or process for cooling the surface of the tissue target site is unique in the incorporated reference in that the cooling body becomes part of the optical pathway through which the infrared energy must pass in order to be recorded.

To improve the S/N in the measurement it is advisable to repeatedly observe the depth selective spectral emissions. A mechanical device designed in accordance with the principles of the incorporated reference to repetitively and repeatably cool and re-heat the target tissue area provides the capability to rapidly cycle between heating and cooling with a typical cycle time of between 0.2 and 5 seconds.

Quantification of the substances of interest is derived from the relative energy emitted through a gradient enhancement technique. To quantify the amount of the substance of interest, a ratio method employs the relative energy emitted at a wavelength known to be absorbed by that substance normalized by the absorption at one or more reference wavelengths.

Figure 6A:
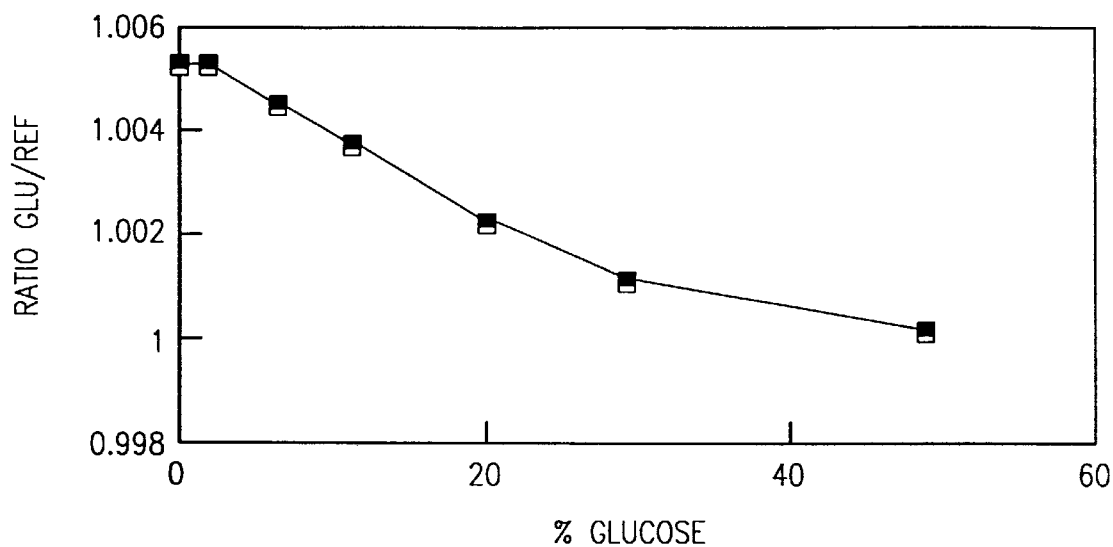
FIGS. 6A and 6B contain two graphs showing the ratio of analytical band energy/reference band energy vs. constituent concentration, and the analytical and reference bands superimposed on the infrared energy spectra in accordance with FIG. 3.
Figure 6B:
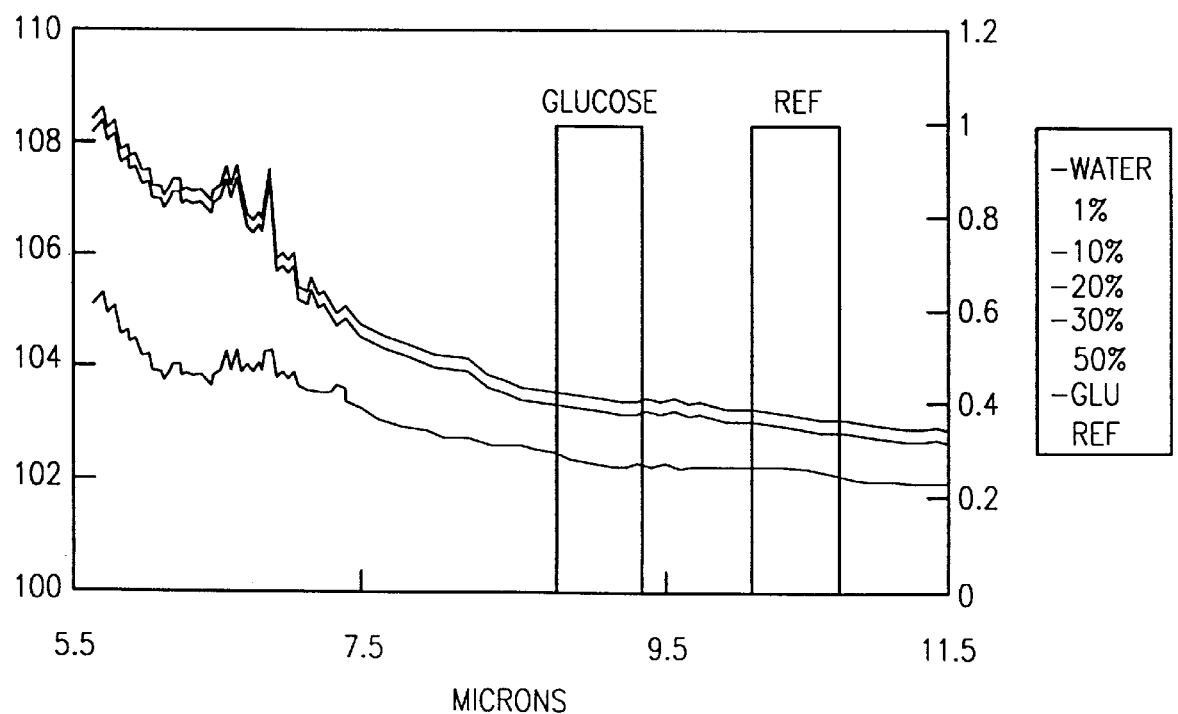

The ratio of analytical band energy/reference band energy is plotted vs. Constituent concentration in the curve shown in FIG. 6. The upper portion of this figure shows the relationship between the emitted energy ratios and the concentration of the analyte. The lower portion of the figure shows the emitted energy vs. wavelength for several concentrations of glucose and the glucose and reference analytical bands used. This relationship is the previously discussed Beer's Law.

It is a particularly noteworthy and novel feature of the present invention is that it obviates the necessity to explicitly measure×(path length) to compute useful glucose concentrations. For example, metabolic glucose concentrations are expressed in mg/dL or milligrams of glucose per 100 milliliters of fluid. Thus, what is actually required is not an absolute measurement of glucose molecules but a ratio of the concentration of glucose to the concentration of other fluid molecules, e.g., water, per unit volume.

While the succeeding discussion centers on the measurement of water and glucose in interstitial fluid, those having ordinary skill in the art will appreciate that the principles presented herein can also modified to measure other interstitial fluid components and analytes of interest including, but specifically not limited to proteins, alcohol, and pharmacological agents. Examination of the absorption spectra reveal that water has characteristic absorption bands near 6.1 and 12 microns, proteins absorb from 6.0 to 8.4 microns and glucose absorbs from 8.5 to 10.0 microns. Using these absorption bands one can compute the relative concentration of each species by rationing. The ratio of glucose concentration to water concentration yields a representation of glucose in mg/dl.

Figure 7:
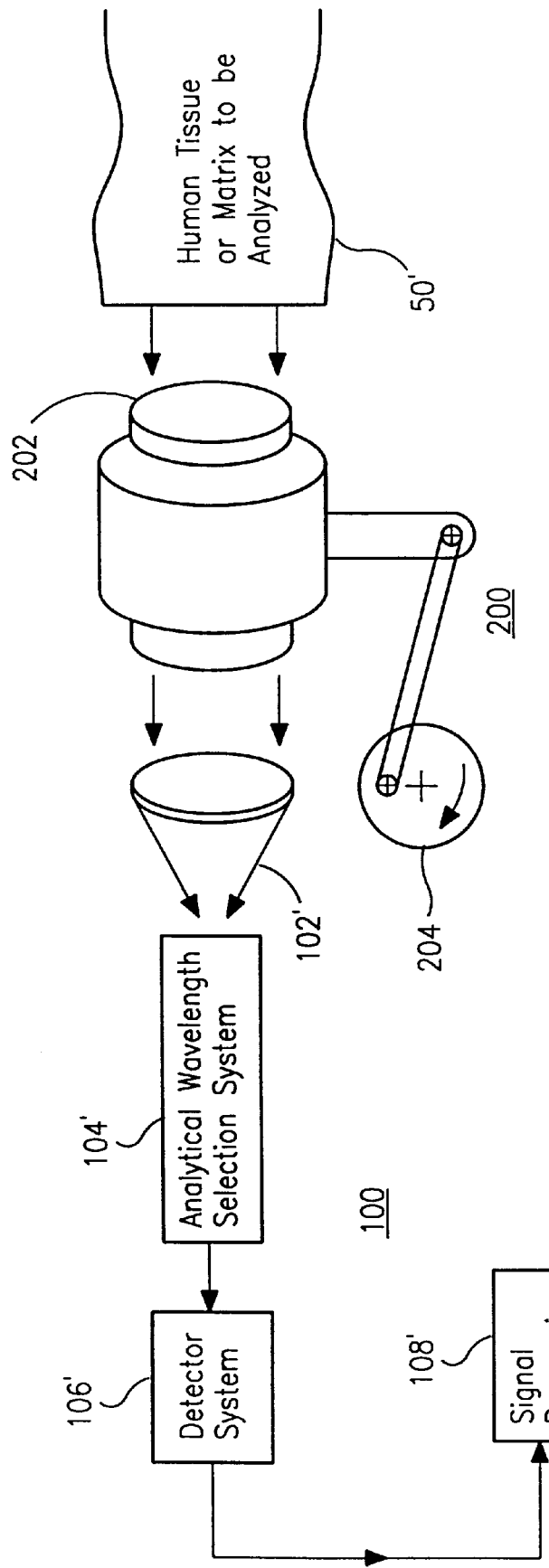
FIG. 7 is an embodiment of a spectrometer implementing the present invention.

The operation of one device capable of performing the present invention is shown at FIG. 7. Referring now to that figure, what is shown is an embodiment of such a system 100. In this embodiment, a thermal gradient inducer 200 induces a temperature gradient within the body 50, and infrared emissions from the body are collected by an optical collector 102. The inducer 200 includes chilling mechanism 202, which repeatedly contacts the body 50' through a reciprocating mechanism 204. In one embodiment, the chilling mechanism 202 is brought into contact with a body. Also in one preferred embodiment, the chilling mechanism is a chilled germanium crystal. The germanium material allows the infrared energy to pass through the chilling mechanism and into the optical collector while still contacting the body and enhancing the temperature gradient. Utilizing this system after each contact of the chilling mechanism with the body 50 an optical measurement is made by the system 100 and the measurements averaged over several contact cycles.

A particular wavelength is selected that corresponds to a particular constituent in the body 50, by a wavelength selection system 104. A detector 106 receives information from the selection system 104. A signal processing system 108 processes the information. The information may then be transmitted, for instance as an electrical signal to other display devices or diagnostic devices. The various elements of the system are as described below.

Analytical Wavelength Selection System 104

Several means of selecting the analytical wavelengths can be used such as:

Discrete infrared bandpass filters

An interferometer

A spectrophotometer

A grating monochrometer

A variable filter monochrometer

In one preferred embodiment a set of 9 discrete analytical filters are used. In an alternate embodiment a PERKIN ELMER (England) System 2000 Fourier Transform Infra Red Spectrophotometer (FTIR) is used in place of the filters. The filters provide a compact system that is rugged and relatively economical. The use of a specific set of bandpass filters restricts the instrument to analyzing only pre selected wavelengths. The use of the FTIR allows the optical measurements of all wavelengths. When using an FTIR the final analysis wavelengths are selected in the signal processing computer. Therefore an instrument built with discrete filters is dedicated to measuring a predetermined compound, e.g. glucose, while an instrument built using an FTIR can be directed via software modifications to measure any of a number of compounds such as glucose, alcohol, etc.

Detector System 106

The detector system converts the infrared energy into usable electrical signals. The detector system 106 typically comprises of two components, an infrared detector and a pre-amplifier.

Signal Processing System 108

The signal processing system 108 used in the preferred embodiment is a personal computer (PC) Others can be substituted with equal facility. The computer provides a computation engine, display and user interface to the system. An analog to digital converter system may be incorporated into signal processing system 108 to interface the analog signals from the detector to the computer.

Chilling Mechanism 202

In a preferred embodiment the chilling mechanism 202 is a germanium crystal which is manufactured by Meller Optics of Providence, R.I. It is 0.75" diameter and 0.75" long. Both end surfaces are "polished to optically flat condition". Other materials, geometries and sizes are acceptable. The crystal's function is twofold. One is to cool the measurement "site", and the other is to efficiently collect and transmit the infrared energy to the collector and detector systems.

The germanium crystal is chilled by a water cooling jacket to approximately 10 Deg. C. This temperature provides an enhanced temperature gradient at the measurement site to enhance the infrared signal to allow detection by conventional detectors. The cooling jacket is typically a water jacket operated at 10° C.

After the germanium crystal contacts the measurement site the proper gradients exist for approximately 500 ms. After that time the crystal is removed and the site re-warmed.

Reciprocating Mechanism 202

In a preferred embodiment, movement of the crystal is accomplished by a cam and lever mechanism driven by a gear head motor. Other mechanisms could be substituted. The requirement is only that the crystal be moved ⅛" to ¼" away from the skin to allow re-warming.

Re-Warming can be also accomplished passively by simply allowing the body to re-warm itself by means of local blood flow to the measurement site. Initial body surface temperatures are typically 30° C. and after 500 ms of chilled crystal contact the skin surface cools to about 20° C. Natural re-warming will take approximately 15 seconds. As a further alternative, the re-warming can be accelerated by blowing warm air at the measurement site or bringing the measurement site in contact with a warm conductive surface.

The surface or air temperature should not exceed 50° C. to avoid discomfort. Optical methods of re-warming by directing infrared, UV or visible light at the measurement site are also applicable. Alternate re-warming means may include ultrasound or microwave. Unlike the cooling means the re-warming mechanism of the present invention need not be infrared transmissive since no signals are measured during the re-warming phase of the cycle. The time of contact with or exposure to the re-warming source is determined by the time required to raise the temperature of the target site tissue from the cooled temperature, to approximately 41° C.

After the surface has been re-warmed to between 30 and 40° C. the measurement cycle can be repeated. In one embodiment, up to 100 cycles will be used to constitute a determination of blood glucose level.

When the crystal is in contact with the patient's skin, infrared energy in the 3 to 15 micron band passes from the skin through the crystal and into the dispersive element of the system. The purpose of the dispersive element is to select analytical wavelengths. With the proper wavelengths selected the computation of glucose concentrations based on the theory described above can be accomplished. A typical operating sequence is shown below.

Operating Sequence

Step 1. Bring instrument in contact with patient's forearm.

Step 2. Reciprocating mechanism brings chilled crystal in contact with patient's skin for 500 ms Step 3. Optical energy is detected, selected, and analyzed by the system signal processor to determine glucose concentration per the formulae discussed below.

Step 4. Reciprocating mechanism removes crystal from skin.

Step 5. Skin re-warms.

Step 6. After skin has re-warmed to approximately 30 to 40 Deg. C., the cycle is repeated until a significant number, e.g., 100, separate glucose determinations have been made.

Step 7. Average all 100 measurements.

Step 8. Transmit resultant concentration determination as an electrical signal to a display device or other device or implement which will then use the measurement for further processing, reporting, or diagnostic purposes. Alternatively, the concentration determination may be transmitted at the end of Step 3, without the averaging performed in steps 4–7.

The concentration determination of step 3 is shown in FIGS. 8–11. Recall now that at any wavelength the total infrared emission $I_t$ reaching detector of an infrared spectrometer, can be defined as:

$$I_t = I_i + I_r + I_s + (I_0 * T),$$

Any radiometer needs calibrating. This includes the calibration of the detector transfer function. Accordingly, $I_i$ and $I_r$ are the instrument dependent variables which must be calibrated out. To accomplish these ends, and in accordance with one preferred embodiment of the present invention, calibration is accomplished by measuring a blackbody-type emitter at two temperatures that bracket the range of temperatures in the thermal gradient tests. For measurements in human skin, calibration at temperatures of 20° C. and 45° C. are adequate. A wavenumber or wavelength range-specific linear correlation function to the theoretical emission based on Planck's equation is established. That correlation function is used subsequently to convert actual test data to data that is calibrated in $mWatts/cm^2/\mu m$.

Figure 8A:
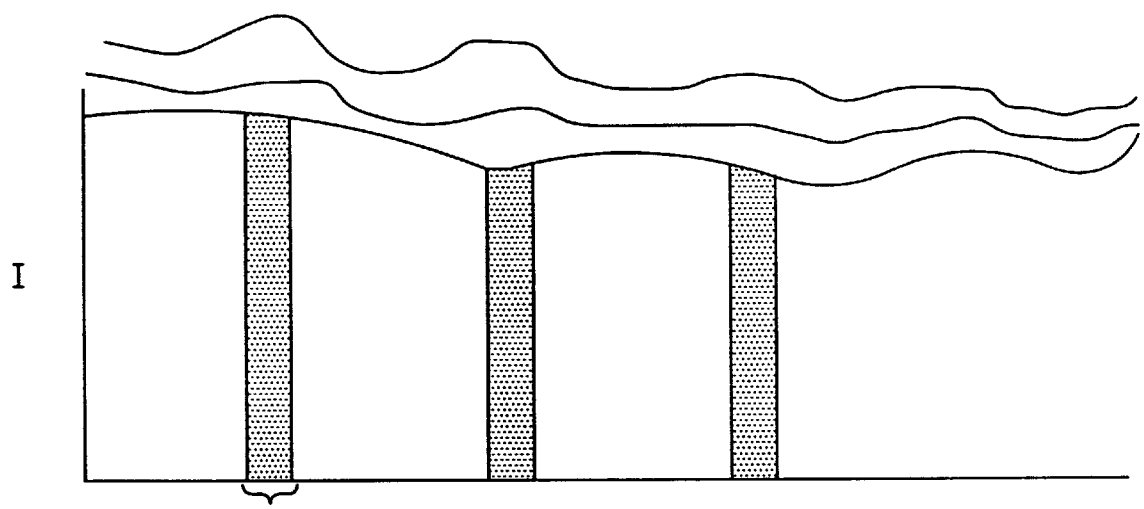
FIGS. 8A and 8B show the time course of a thermal event at a single wavelength.
Figure 8B:
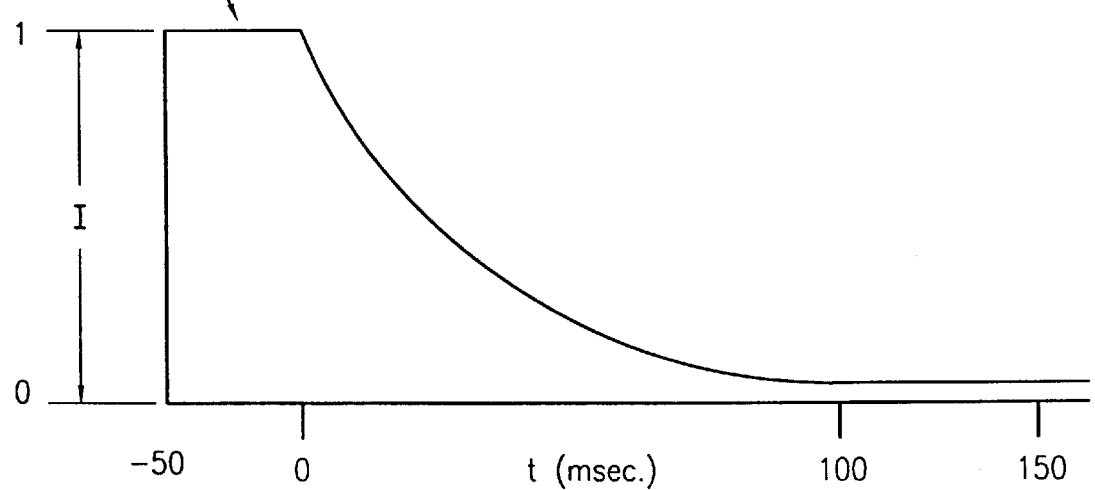
Figure 9:
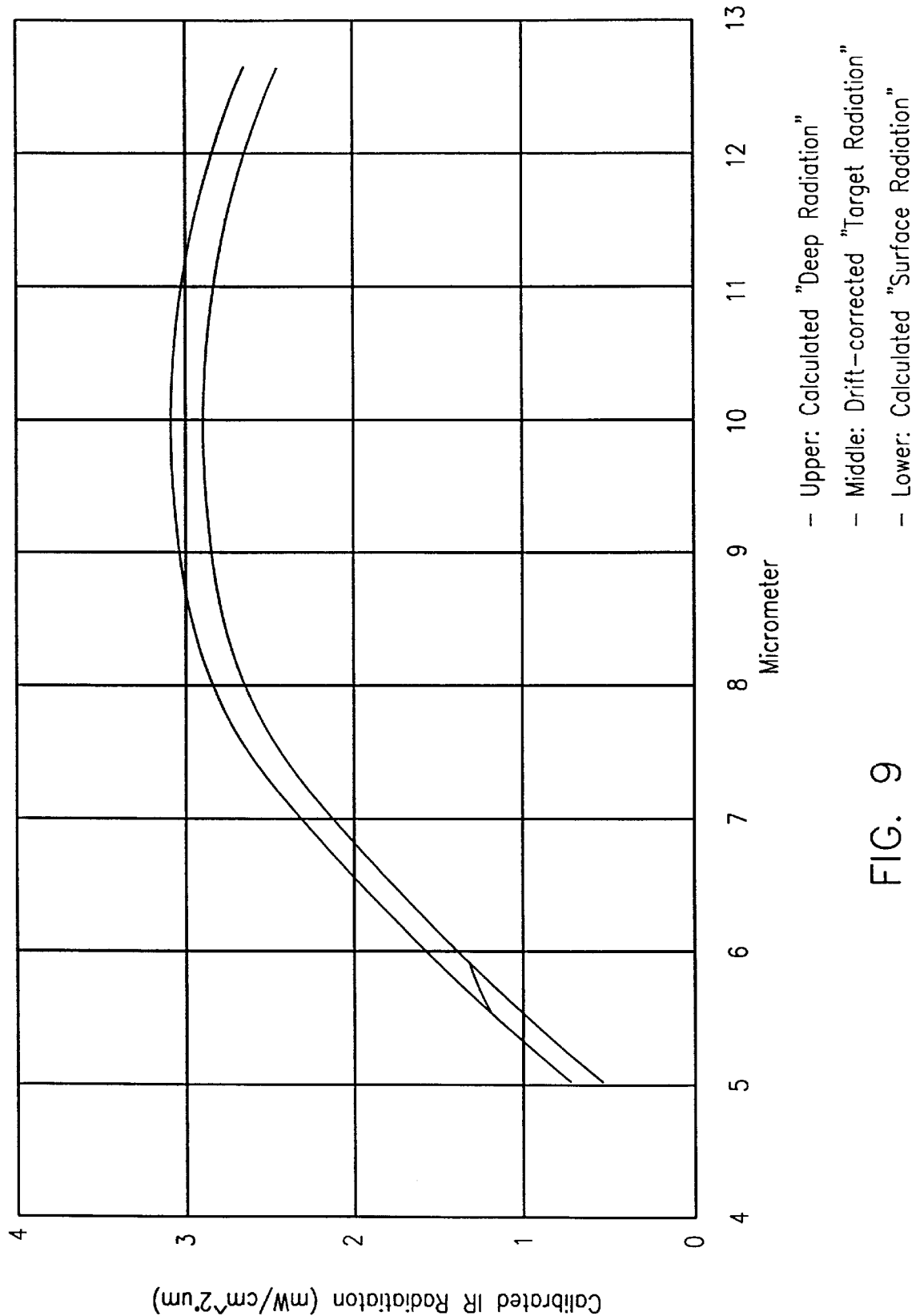
FIG. 9 is a plot of calibrated IR Radiation at all wavelengths from 4–13 micrometers, of the calculated deep radiation $I_0$, drift corrected target radiation, and calculated surface radiation $I_s$.
Figure 10:
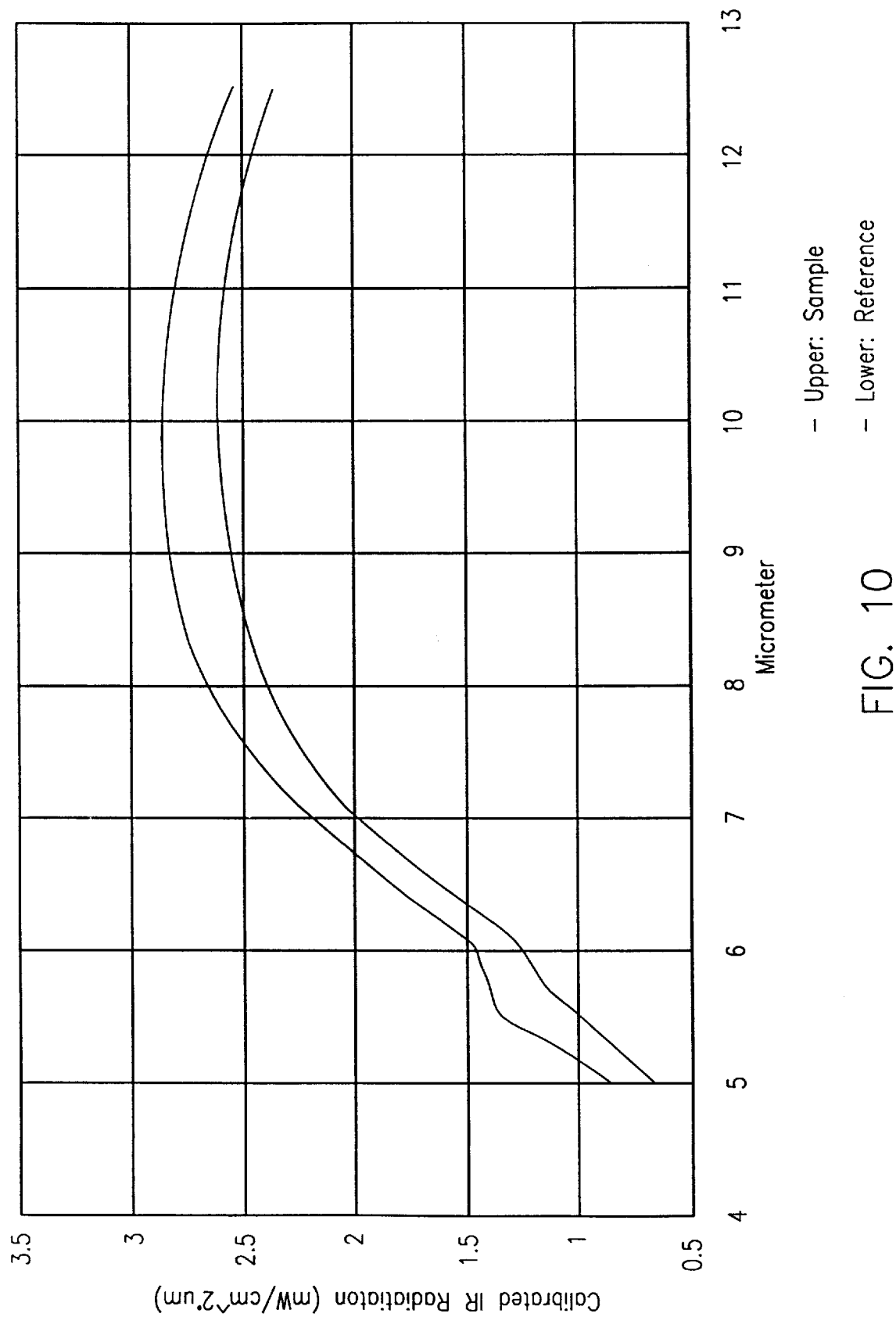
FIG. 10 is a plot of IR Radiation at all wavelengths from 4–13 micrometers showing the detector output, after calibration, for a sample and a reference.

Further, the short term instrument drift must be corrected for. In general short-term instrument drift is corrected best when the signal is chopped into very short time segments and intercalated with a reference signal. The difference between the two signals is then amplified and background intensity variation that is slower than the chopping rate is largely eliminated. Time-resolved thermal gradient spectrometry offers the opportunity for such fast referencing and very short-term instrument drift correction. Once the surface begins to cool down, the thermal gradient penetrates into a material such as skin, maximal absorption by the cooled layers is reached after about one hundred milliseconds. The total cycle time for heating and cooling is typically one minute, and may be less than five seconds. The entire cooling part of the cycle can be chopped into smaller time segments by, for instance, taking a scan or data point every 1 to 16 ms, e.g. by a multi-detector system. Integrated data from late time segments can serve as reference for earlier ones because they 1) have almost identical instrument and predictable target surface emission intensity components and 2) differ from the earlier data essentially only in the steepness of the thermal gradient. Typically, instrument drift over fractions of a second is negligible compared to the drift over a substantially longer period, such as the time since the last calibration step. Another advantage of such a gradient run-internal drift correction mechanism is its simplicity. No changes need to be made to the measurement system and apparatus to effect such a drift-correcting reference measurement. Several referencing schemes are possible: Referring now to FIG. 8, data taken at 100 to 150 ms can provide the drift correction for a scan taken at 5 to 50 ms, or an average of data taken from 5 to 150 ms can be drift corrected by an average of data taken anywhere between 350 ms and 1 s. Optimally, the number of reference scans or integrated segments is somewhat larger than the number of sample scans or segments. Such a referencing scheme is novel and very useful in that it can reduce instrument noise by orders of magnitude. The drift correction can be implemented as a subtraction step at the primary radiation intensity level. A calculated best-fit blackbody emission curve, according to Planck's equation is calculated based on the average reference scan over the entire range or a fraction thereof, see FIG. 9. The difference at all wavenumber or wavelength segments between the reference scan and the calculated Planck function is then calculated and applied to the sample scan or average. This process results in a sample scan from which nearly all instrument and non-specific sample material contributions have been subtracted. Essentially all that is left is blackbody emission from the surface and from the deeper layers modified by the desirable absorption of constituents.

In a first alternative short-term drift correction methodology, a simple ratio can be utilized of sample data over reference data which have been taken at a later time during thermal gradient development. The result will be a sloping transmittance scan that can be corrected for residual temperature effects as disclosed below.

In a second alternative short-term drift correction methodology, a chopped system can be employed that intercalates a blackbody emitting reference material of known temperature with test material. Such a system is mechanically more complex and the temperature measurement accuracy needed is limiting the accuracy of a constituent determination.

In a third alternative short-term drift correction methodology, the data points taken immediately before cooling the surface can be used as reference emission intensities. This is optimal only in technical implementations without optical interface changes when physical contact is established. The radiative target surface temperature may be calculated to represent the temperature after surface cooling has started.

The previously discussed steps of instrument calibration and short-term instrument drift correction can be combined in another preferred embodiment of the present invention. Time-resolved thermal gradient spectroscopy offers a unique and powerful combination of instrument calibration and drift correction. Pre-contact high temperature (e.g. at 40 degrees Celsius) data and End-of-contact low temperature (e.g. 5 degrees Celsius) data can be used as the calibration and drift correction sets at the same time. A linear correlation (slope and offset) is calculated, for every data point in time at every wavelength range, from these two data sets and from two corresponding blackbody (BB) data sets at the pre-contact and end-of-gradient temperatures:

$$\text{Slope:}(\text{Watts}_{BB\ high} - \text{Watts}_{BB\ low})/(\text{Volts}_{Pre\text{-}contract} - \text{Volts}_{End\text{-}of\text{-}gradient})$$

$$\text{Offset:}(\text{Watt}_{BB\ high} - (\text{Volts}_{End\text{-}of\text{-}gradient} * \text{Slope})$$

and applied to any data set during the thermal gradient by multiplying with "Slope" and adding "Offset". This operation provides ideal blackbody boundary conditions and thereby essentially eliminates all instrument artifacts. The precontract and end-of-gradient temperatures can be physically measured with temperature probes. Time-resolved wattage data can now be zeroed and spanned to their respective pre-contact and end-of-contact Planck wattage equivalent, see FIG. 10.

Finally, the percent transmittance of a plurality, n, of analytes under analysis can be calculated. The short-term instrument drift correction disclosed above results in corrected sample data that are still strongly affected by the actual temperature of the sample target. The relative contribution can vary significantly between repeat tests. For a low level constituent such as glucose in tissue, at a total concentration of 0.08% under normal physiological conditions, accurate temperature effect correction is important because that effect can overshadow the optical effect produced by the entire physiological range. In addition to temperature effect removal, the transmittance measurement needs to be standardized, zeroed and spanned to 100% transmittance, just like single beam optical instruments have to be standardized. By definition 0% transmittance occurs at any wavelength range where one or more components are so strongly absorbing that no radiation from the deeper layer can penetrate to the surface and reach the detector. At that wavelength range any emission is by definition coming from the surface; i.e., the emission at that wavelength range is the surface emission intensity $I_s$. Once determined at one or more specific wavelength ranges, one can calculate the 0% transmittance baseline at all wavelengths. For largely aqueous systems excellent wavelength ranges are found at about 6.1 and 12 μm. The optical depth is less than 1 μm into tissue at 6.1 μm. A theoretical best-fit blackbody curve is calculated through one or more such wavelength ranges. The resulting data set is the 0% transmittance line. This line represents the emission exclusively from the surface at any wavelength. In order to identify the "100% span" for the transmission data set, a wavelength range is needed where the transmission layer(s) are substantially more transmissive than at other analytical wavelength ranges. For largely aqueous systems an excellent range is 5 to 5.5 μm. Other wavelength ranges of relative maximal transmittance can be similarly utile. Examples of the latter are 6.75 μm, 10.4 μm, or 8.4 μm. Ideally, the relative percentage of constituents absorbing at that range is constant, so that a percentage of factor can be applied in case the transmittance is less than 100% in order to truly span to 100%. For water-based systems, this ideal situation is largely the case because water is the dominant absorbing constituent. A theoretical best-fit blackbody curve is then calculated through this wavelength range, The resulting data set constitutes $I_s + I_0$. The surface emission $I_s$ is subtracted leaving only $I_0$ at all wavelengths. The surface emission is also subtracted from the sample emission intensity I of the entire sample data set. Transmittance is obtained by dividing the resulting difference by $I_0$ at all wavelengths.

$$T = \frac{I - I_S}{I_O - I_S}$$

In some embodiments, transmittance may be satisfactorily approximated using the formula $$T = \frac{I - I_S}{I_O}.$$

This approximation may be especially utile where the surface emission is of similar magnitude as the reference intensity.

It will be appreciated that all instrument drift effects, sample material-instrument interface effects and surface emission effects are substantially eliminated. The result is a sufficiently clean transmittance spectrum that can be converted to an absorption (optical density) as discussed below. This spectrum can then be scaled and normalized or otherwise manipulated like a conventional IR-spectrum.

A solution to the path length problem comes from the convention that constituents such as glucose (or blood alcohol) are needed as relative quantities whereas the absolute magnitude is not needed separately. The concentration is typically defined as amount of glucose in mg per volume of fluid in mL. The fluid in this case is water and fortunately, it too has a strong IR absorption at wavelengths where other constituents have little absorbance. One such useful range for relative water determination is between 10.5 and 12 μm. In a ratio of say, glucose absorbance over water absorbance, the 1 term cancels and one obtains an optical expression for amount glucose per amount water, that can be calibrated in terms of mg/dL. An internal reference is identified that allows for elimination of the pathlength term in the equation above.

Other wavelength ranges can be similarly useful in the determination of water in the material. The relative plateau from about 7 to 10 μm is useful for a relative water determination at any wavelength where constituents other than water show relatively little absorbance. Alternatively, the constituent of interest can be related to one other major constituent that is essentially constant in its relative amount. Total protein is such a candidate; it shows several strong absorbencies in the wavelength range from about 6 to 8 μm. Particularly in skin, total protein is not expected to change much.

Recalling Beer's Law, the elimination of the path length from the determination of the ratio of concentrations of glucose and water is thus explained:

$$\frac{I}{I_0} = e^{-\beta cL}$$

which can be restated:

$$\log\left(\frac{I}{I_O}\right) = -\beta cL$$

which, for any given analyte in a system of n analytes, can in turn be further restated as:

$$c = \frac{-\log\left(\frac{I}{I_O}\right)}{\beta L}$$

Hence, given a ratio of n analytes, in this case two analytes which are components of body fluid, glucose and water, the ratio of their concentrations can further be shown to be:

$$\frac{c_{glucose}}{c_{water}} = \frac{\log\left(\frac{I^{glucose}}{I_0^{glucose}}\right)}{\beta^{glucose} L} \bigg/ \frac{\log\left(\frac{I^{water}}{I_0^{water}}\right)}{\beta^{water} L}$$

hence, algebraically:

$$\frac{c_{glucose}}{c_{water}} = \frac{\log\left(\frac{I^{glucose}}{I_0^{glucose}}\right) \beta^{water}}{\log\left(\frac{I^{water}}{I_0^{water}}\right) \beta^{glucose}}$$

It will be appreciated that in the latter form of the equation the pathlengths L have algebraically cancelled out, thereby providing the parameter needed to express the ratio of the concentrations of the analytes independent of the path length under analysis.

Figure 11:
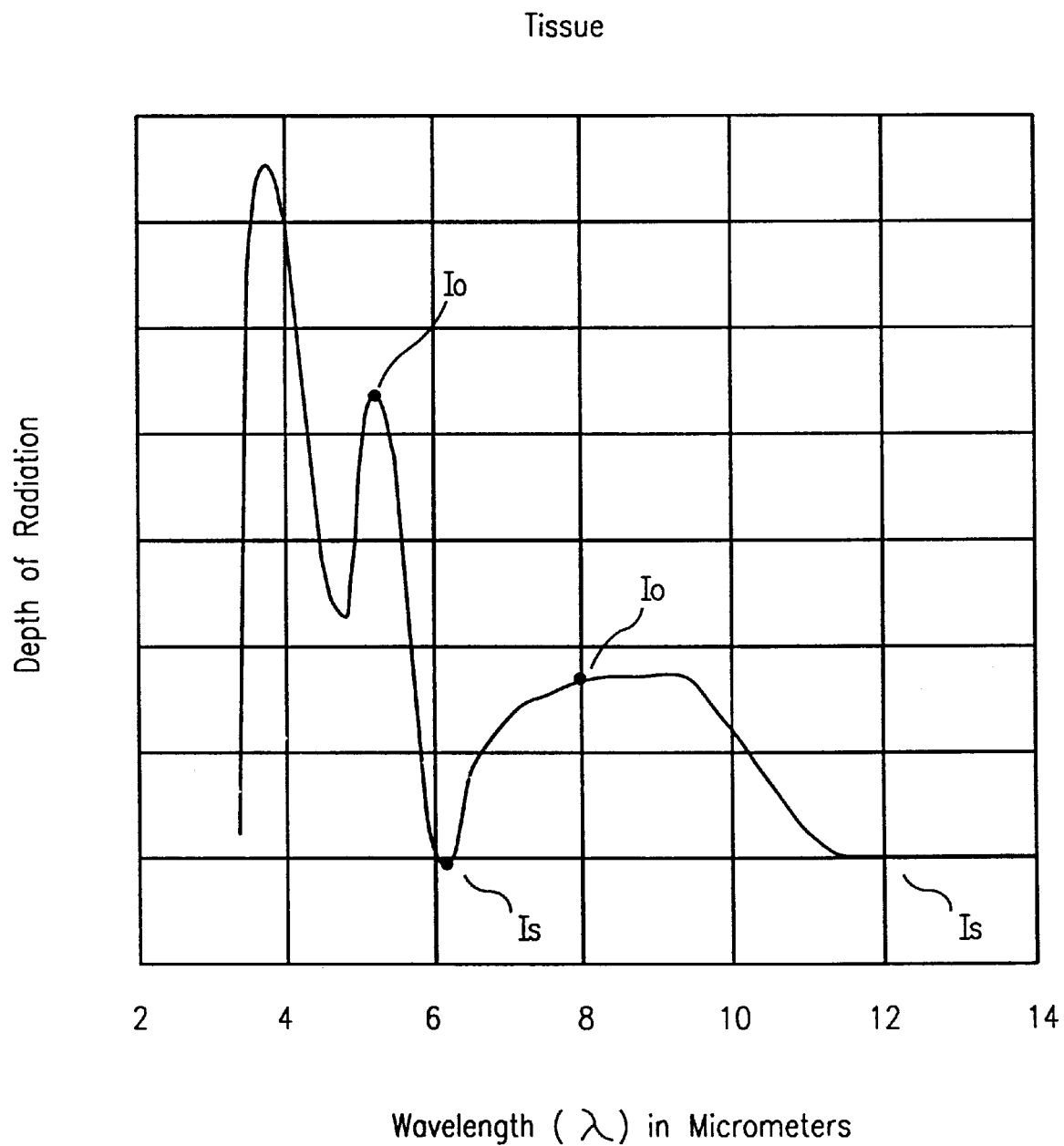
FIG. 11 is a graph of the depth of infrared radiation in tissue over a range of wavelengths from 2–14 micrometers, demonstrating the semi-empirical method of selecting a wavelength for $I_0$ and $I_s$ calculations.

The present invention discloses semi-empirical approaches that are useful in general for the reduction to conventional data or transmittance spectra, as shown in FIG. 11. The procedure has been optimized for systems that contain large relative amounts of water. There is wider applicability to homogeneous and especially heterogeneous and layered materials providing that useful wavelength ranges can be identified: 1)for $I_0$ determination, one or more wavelength ranges where the optical depth is small and 2) for $I_s$ determination, one or more wavelength ranges where the optical depth is large. Ideally, the effective thermal gradient depth is selected for a) 100% transmittance at one or more reference wavelength ranges while giving sufficient optical depth at the wavelength ranges used for analysis, and b) 0% transmittance at one or more other wavelengths ranges. For largely aqueous systems useful ranges are around 6.1 μm and about 12 μm and higher for 0% transmittance determination and 5 to 5.5 μm or alternatively one or more ranges in the relative plateau from about 7 to 10 μm for 100% transmittance calculation. A wavelength range centered at 8 μm is useful for relatively low tissue absorption.

From the foregoing it will be obvious to those having ordinary skill in the art that the application of the principles taught herein provide one or more of the following advantages:

provide a method for analyzing liquid or solid, including semi-solid such as biologicals. It is not limited to, but is specifically well suitable for living tissue;

provide a method for improving the resolution over prior thermal gradient spectrometric methodologies by one or more orders of magnitude;

provide a non-invasive method for either determining low levels of constituents and/or alternatively measuring high levels very accurately;

provide a method for determination of penetration depth of thermal gradient into material for sufficient optical depth development;

provide for the quantitative determination of at least one component in the material;

provide data that are substantially free of measuring instrument artifacts;

provide data that are quantitatively representative of the composition of the material, for example optical density at any wavelength should be the linear or non-linear combination of optical densities of individual components as it is well known in conventional optical absorption spectroscopy. In the simplest case it should follow Beer's law;

provide specific reference wavelengths that are optimal for aqueous systems, specifically human tissue, for the reduction of transient or steady-state thermal transmission spectra to conventional transmission spectra;

measure accurately low analyte(s) concentration(s), for example glucose in body fluids at 100 mg/dL or blood alcohol at 0.1%;

measure at high repeat precision, for example at 1 to 5% of normal analyte levels within an acquired data set;

provide a difference function for short-term instrument drift correction after every cooling cycle;

measure at shallow thermal gradients, for example starting under 42° C. before cooling the surface and ending at over 0° C. after cooling as required for non-invasive in vivo measurements;

determine appropriate wavelengths(s) and develop an methodology to measure the water content in the sample so that the amount of constituent of interest can be expressed as concentration, for example as mg glucose per dL of body fluid;

provide methodology that gives correction for the continually variable optical pathlength as the thermal gradient progresses into material;

provide method that gives correction for the continually variable blackbody intensity/optical pathlength integral of the deeper layers as the thermal gradient progresses into material;

provide method for determination of the effective deeper layer blackbody-equivalent emission temperature at all wavelengths;

provide method for determination of the effective surface layer blackbody-equivalent emission temperature at all wavelengths;

define useful wavelengths ranges for the reduction of Transient or Steady-state Thermal Gradient Transmission data to conventional calibrated transmission data;

define one or more useful wavelength ranges for internal calibration;

define combination and sequencing of scan information to provide best overall instrument drift compensation, intra-gradient radiometric artifact ejection and intergradient referencing;

define independent measurement technologies to confirm the existence, timing, wavelength ranges and optimal sampling strategies to recover transient thermal gradient emission information.

The present invention has been particularly shown and described with respect to certain preferred embodiments of features thereof. However, it should be readily apparent to those of ordinary skill in the art that various changes and modifications in form and detail may be made without departing from the spirit and scope of the invention as set forth in the appended claims. The invention disclosed herein may be practiced without any element which is not specifically disclosed herein.

What is claimed is:

1. A method for spectroscopically analyzing a material utilizing a spectrometric instrument and a means for inducing a thermal gradient in said material, comprising the steps of:

(a) inducing said thermal gradient in said material;

(b) responsive to said inducing step, determining the surface emission from the material; and (c) determining a parameter from said surface emission correlating to a property of said material independent of optical pathlength.

2. A method as recited in claim 1, further comprising the steps of:

(d) determining a reference intensity from said material; and (e) determining said parameter correlating to a property of said material from said surface emission and said reference intensity.

3. A method as recited in claim 2, wherein said reference intensity is determined utilizing said spectrometric instrument.

4. A method as recited in claim 1, further comprising the step of calibrating said instrument prior to said inducing step.

5. A method as recited in claim 1, further comprising the step of transmitting said parameter correlating to a property of said material as an electrical signal for further processing.

6. A method for spectroscopically analyzing a material utilizing a spectrometric instrument and a means for inducing a thermal gradient in said material, comprising the steps of:

(a) determining a reference intensity from said material; and (b) inducing said thermal gradient in said material;

(c) responsive to said inducing step, determining the surface emission from the material; and (d) determining a parameter correlating to a property of said material from said surface emission and said reference intensity.

7. A method as recited in claim 6, wherein said reference intensity is determined utilizing said spectrometric instrument.

8. A method as recited in claim 6, wherein said parameter correlating to a property of said material is determined independent of optical pathlength.

9. A method as recited in claim 6, further comprising the step of calibrating said instrument prior to said inducing step.

10. A method as recited in claim 6, further comprising the step of transmitting said parameter correlating to a property of said material as an electrical signal for further processing.

11. A method for spectroscopically analyzing a material utilizing a spectrometric instrument and a means for inducing a thermal gradient in said material, comprising the steps of:

(a) determining a reference intensity from said material utilizing said spectrometric instrument;

(b) inducing said thermal gradient in said material;

(c) responsive to said inducing step, determining the surface emission from the material; and (d) determining a parameter correlating to a property of said material from said surface emission and said reference intensity.

12. A method as recited in claim 11, wherein said parameter correlating to a property of said material is determined independent of optical pathlength.

13. A method as recited in claim 11, further comprising the step of calibrating said instrument prior to said inducing step.

14. A method as recited in claim 11, further comprising the step of transmitting said parameter correlating to a property of said material as an electrical signal for further processing.

15. A method for spectroscopically analyzing a material utilizing a spectrometric instrument and a means for inducing a thermal gradient in said material, comprising the steps of:

(a) calibrating said spectrometric instrument;

(b) inducing said thermal gradient in said material;

(c) responsive to said inducing step, determining the surface emission from the material; and (d) determining a parameter from said surface emission correlating to a property of said material.

16. A method as recited in claim 15, wherein said parameter correlating to a property of said material is determined independent of optical pathlength.

17. A method as recited in claim 15, further comprising the steps of:

(e) determining a reference intensity from said material; and (f) determining said parameter correlating to a property of said material from said surface emission and said reference intensity.

18. A method as recited in claim 17, wherein said reference intensity is determined utilizing said spectrometric instrument.

19. A method as recited in claim 15, further comprising the step of transmitting said parameter correlating to a property of said material as an electrical signal for further processing.

20. A method for spectroscopically analyzing a material utilizing a spectrometric instrument and a means for inducing a thermal gradient in said material, comprising the steps of:

(a) inducing said thermal gradient in said material;

(b) responsive to said inducing step, determining the surface emission from the material;

(c) determining a parameter from said surface emission correlating to a property of said material; and (d) transmitting said parameter as an electrical signal for further processing.

21. A method as recited in claim 20, wherein said parameter correlating to a property of said material is determined independent of optical pathlength.

22. A method as recited in claim 20, further comprising the steps of:

(e) determining a reference intensity from said material; and (f) determining said parameter correlating to a property of said material from said surface emission and said reference intensity.

23. A method as recited in claim 22, wherein said reference intensity is determined utilizing said spectrometric instrument.

24. A method as recited in claim 20, further comprising the step of calibrating said instrument prior to said inducing step.

* * * * *